United States Patent
Zarins et al.

(10) Patent No.: US 10,034,708 B2
(45) Date of Patent: Jul. 31, 2018

(54) METHODS AND APPARATUS FOR THERMALLY-INDUCED RENAL NEUROMODULATION

(71) Applicants: Denise Zarins, Saratoga, CA (US); Andrew Wu, Los Altos Hills, CA (US); Hanson Gifford, III, Woodside, CA (US); Mark Deem, Mountain View, CA (US); Mark Gelfand, New York, NY (US); Howard R. Levin, Teaneck, NJ (US)

(72) Inventors: Denise Zarins, Saratoga, CA (US); Andrew Wu, Los Altos Hills, CA (US); Hanson Gifford, III, Woodside, CA (US); Mark Deem, Mountain View, CA (US); Mark Gelfand, New York, NY (US); Howard R. Levin, Teaneck, NJ (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 310 days.

(21) Appl. No.: 14/737,254

(22) Filed: Jun. 11, 2015

(65) Prior Publication Data
US 2015/0282877 A1 Oct. 8, 2015

Related U.S. Application Data

(63) Continuation of application No. 14/094,330, filed on Dec. 2, 2013, now abandoned, which is a continuation
(Continued)

(51) Int. Cl.
*A61B 18/14* (2006.01)
*A61F 7/12* (2006.01)
(Continued)

(52) U.S. Cl.
CPC .......... *A61B 18/1492* (2013.01); *A61F 7/123* (2013.01); *A61M 5/14276* (2013.01);
(Continued)

(58) Field of Classification Search
CPC .............. A61N 5/045; A61M 5/14276; A61M 2210/1082; A61B 18/1492; A61B 2018/00511; A61B 2018/00505
See application file for complete search history.

(56) References Cited

U.S. PATENT DOCUMENTS

| 2,130,758 A | 9/1938 | Rose |
| 2,276,995 A | 3/1942 | Milinowski |

(Continued)

FOREIGN PATENT DOCUMENTS

| CA | 2384866 | 4/2001 |
| CA | 2575458 | 3/2006 |

(Continued)

OTHER PUBLICATIONS

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
(Continued)

*Primary Examiner* — Bradley J Osinski

(57) ABSTRACT

Methods and apparatus are provided for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neu-
(Continued)

romodulation. In some embodiments, protective elements may be provided to reduce a degree of thermal damage induced in the non-target tissues. In some embodiments, thermally-induced renal neuromodulation is achieved via delivery of a pulsed thermal therapy.

25 Claims, 15 Drawing Sheets

Related U.S. Application Data of application No. 13/046,595, filed on Mar. 11, 2011, now Pat. No. 8,626,300, which is a continuation of application No. 11/599,723, filed on Nov. 14, 2006, now abandoned, which is a continuation-in-part of application No. 10/408,665, filed on Apr. 8, 2003, now Pat. No. 7,162,303, said application No. 11/599,723 is a continuation-in-part of application No. 11/189,563, filed on Jul. 25, 2005, now Pat. No. 8,145,316, which is a continuation-in-part of application No. 11/129,765, filed on May 13, 2005, now Pat. No. 7,653,665, said application No. 11/599,723 is a continuation-in-part of application No. 11/504,117, filed on Aug. 14, 2006, now Pat. No. 7,617,005.

(60) Provisional application No. 60/816,999, filed on Jun. 28, 2006, provisional application No. 60/370,190, filed on Apr. 8, 2002, provisional application No. 60/415,575, filed on Oct. 3, 2002, provisional application No. 60/442,970, filed on Jan. 29, 2003, provisional application No. 60/616,254, filed on Oct. 5, 2004, provisional application No. 60/624,793, filed on Nov. 2, 2004.

(51) Int. Cl.
| | |
|---|---|
| *A61M 5/142* | (2006.01) |
| *A61N 1/28* | (2006.01) |
| *A61N 1/32* | (2006.01) |
| *A61N 1/40* | (2006.01) |
| *A61N 5/04* | (2006.01) |
| *A61N 7/02* | (2006.01) |
| *A61M 5/172* | (2006.01) |
| *A61N 1/36* | (2006.01) |
| *A61N 1/362* | (2006.01) |
| *A61N 7/00* | (2006.01) |
| *A61B 18/00* | (2006.01) |

(52) U.S. Cl.
CPC .......... *A61N 1/28* (2013.01); *A61N 1/32* (2013.01); *A61N 1/326* (2013.01); *A61N 1/36017* (2013.01); *A61N 1/403* (2013.01); *A61N 5/045* (2013.01); *A61N 7/02* (2013.01); *A61B 2018/00404* (2013.01); *A61B 2018/00434* (2013.01); *A61B 2018/00505* (2013.01); *A61B 2018/00511* (2013.01); *A61B 2018/00577* (2013.01); *A61B 2018/00642* (2013.01); *A61F 2007/126* (2013.01); *A61M 5/1723* (2013.01); *A61M 2210/1082* (2013.01); *A61N 1/36007* (2013.01); *A61N 1/3627* (2013.01); *A61N 1/36114* (2013.01); *A61N 2007/003* (2013.01)

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,752,162 A | 8/1973 | Newash |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,824,436 A | 4/1989 | Wolinsky |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,087,244 A | 2/1992 | Wolinsky et al. |
| 5,094,242 A | 3/1992 | Gleason et al. |
| 5,102,402 A | 4/1992 | Dror et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |

(56) References Cited

U.S. PATENT DOCUMENTS

| | | |
|---|---|---|
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |
| 5,306,250 A | 4/1994 | March et al. |
| 5,317,155 A | 5/1994 | King |
| 5,324,255 A | 6/1994 | Passafaro et al. |
| 5,324,316 A | 6/1994 | Schulman et al. |
| 5,326,341 A | 7/1994 | Lew et al. |
| 5,334,193 A | 8/1994 | Nardella |
| 5,335,657 A | 8/1994 | Terry, Jr. et al. |
| 5,338,662 A | 8/1994 | Sadri |
| 5,344,395 A | 9/1994 | Whalen et al. |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,419,767 A | 5/1995 | Eggers et al. |
| 5,419,777 A | 5/1995 | Hofling |
| 5,423,744 A | 6/1995 | Gencheff et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,464,395 A | 11/1995 | Faxon et al. |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,538,504 A | 7/1996 | Linden et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,960 A | 12/1996 | Edwards et al. |
| 5,588,962 A | 12/1996 | Nicholas et al. |
| 5,588,964 A | 12/1996 | Imran et al. |
| 5,589,192 A | 12/1996 | Okabe et al. |
| 5,590,654 A | 1/1997 | Prince |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,667,490 A | 9/1997 | Keith et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,709,874 A | 1/1998 | Hanson et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,817,144 A | 10/1998 | Gregory |
| 5,824,087 A | 10/1998 | Aspden et al. |
| 5,836,935 A | 11/1998 | Ashton et al. |
| RE35,987 E | 12/1998 | Harris et al. |
| 5,843,016 A | 12/1998 | Lugnani et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,865,801 A | 2/1999 | Houser |
| 5,871,449 A | 2/1999 | Brown |
| 5,876,374 A | 3/1999 | Alba et al. |
| 5,891,181 A | 4/1999 | Zhu et al. |
| 5,893,885 A | 4/1999 | Webster et al. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,227 A | 6/1999 | Keith et al. |
| 5,916,239 A | 6/1999 | Geddes et al. |
| 5,919,187 A | 7/1999 | Guglielmi et al. |
| 5,924,424 A | 7/1999 | Stevens et al. |
| 5,924,997 A | 7/1999 | Campbell |
| 5,928,272 A | 7/1999 | Adkins et al. |
| 5,935,075 A | 8/1999 | Casscells et al. |
| 5,938,670 A | 8/1999 | Keith et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 5,989,208 A | 11/1999 | Nita |
| 5,997,497 A | 12/1999 | Nita et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh et al. |
| 6,026,326 A | 2/2000 | Bardy |
| 6,036,687 A | 3/2000 | Laufer et al. |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,117,101 A | 9/2000 | Diederich et al. |
| 6,117,128 A | 9/2000 | Gregory |
| 6,122,548 A | 9/2000 | Starkebaum et al. |
| 6,123,718 A | 9/2000 | Tu et al. |

(56) References Cited

U.S. PATENT DOCUMENTS

| | | |
|---|---|---|
| 6,135,999 A | 10/2000 | Fanton et al. |
| 6,142,993 A | 11/2000 | Whayne et al. |
| 6,146,380 A | 11/2000 | Racz et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,211,247 B1 | 4/2001 | Goodman |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,231,516 B1 | 5/2001 | Keilman et al. |
| 6,238,702 B1 | 5/2001 | Berde et al. |
| 6,245,026 B1 | 6/2001 | Campbell et al. |
| 6,245,045 B1 | 6/2001 | Stratienko |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,283,947 B1 | 9/2001 | Mirzaee |
| 6,283,951 B1 * | 9/2001 | Flaherty ............... A61B 17/11 604/164.11 |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,296,619 B1 | 10/2001 | Brisken et al. |
| 6,302,870 B1 | 10/2001 | Jacobsen et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,309,379 B1 | 10/2001 | Willard et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,379,373 B1 | 4/2002 | Sawhney et al. |
| 6,389,314 B2 | 5/2002 | Feiring |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,484,052 B1 | 11/2002 | Visuri et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,514,236 B1 | 2/2003 | Stratienko |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,274 B1 | 2/2003 | Rosenthal et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,558,382 B2 | 5/2003 | Jahns et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,595,959 B1 | 7/2003 | Stratienko |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,623,452 B2 | 9/2003 | Chien et al. |
| 6,623,453 B1 | 9/2003 | Guibert et al. |
| 6,635,054 B2 | 10/2003 | Fjield et al. |
| 6,640,120 B1 | 10/2003 | Swanson et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,689,086 B1 | 2/2004 | Nita et al. |
| 6,689,148 B2 | 2/2004 | Sawhney et al. |
| 6,690,971 B2 | 2/2004 | Schauerte et al. |
| 6,692,738 B2 | 2/2004 | MacLaughlin et al. |
| 6,695,830 B2 | 2/2004 | Vigil et al. |
| 6,697,670 B2 | 2/2004 | Chomenky et al. |
| 6,699,231 B1 * | 3/2004 | Sterman ........... A61B 17/12045 604/4.01 |
| 6,706,011 B1 | 3/2004 | Murphy-Chutorian et al. |
| 6,711,444 B2 | 3/2004 | Koblish |
| 6,714,822 B2 | 3/2004 | King et al. |
| 6,718,208 B2 | 4/2004 | Hill et al. |
| 6,723,064 B2 | 4/2004 | Babaev |
| 6,735,471 B2 | 5/2004 | Hill et al. |
| 6,738,663 B2 | 5/2004 | Schroeppel et al. |
| 6,749,598 B1 | 6/2004 | Keren et al. |
| 6,752,805 B2 | 6/2004 | Maguire et al. |
| 6,767,544 B2 * | 7/2004 | Brooks ............... A61K 38/4893 424/239.1 |
| 6,786,904 B2 | 9/2004 | Doscher et al. |
| 6,788,977 B2 | 9/2004 | Fenn et al. |
| 6,795,728 B2 | 9/2004 | Chornenky et al. |
| 6,830,568 B1 | 12/2004 | Kesten et al. |
| 6,845,267 B2 * | 1/2005 | Harrison ............... A61N 1/32 604/891.1 |
| 6,849,075 B2 | 2/2005 | Bertolero et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,893,414 B2 | 5/2005 | Goble et al. |
| 6,916,656 B2 | 7/2005 | Walters et al. |
| 6,917,834 B2 | 7/2005 | Koblish et al. |
| 6,923,808 B2 | 8/2005 | Taimisto |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,949,097 B2 | 9/2005 | Stewart et al. |

(56) References Cited

U.S. PATENT DOCUMENTS

| | | |
|---|---|---|
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,991,617 B2 | 1/2006 | Hektner et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,066,904 B2 | 6/2006 | Rosenthal et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,127,284 B2 | 10/2006 | Seward |
| 7,141,041 B2 | 11/2006 | Seward |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,197,354 B2 | 3/2007 | Sobe |
| 7,241,273 B2 | 7/2007 | Maguire et al. |
| 7,241,736 B2 | 7/2007 | Hunter et al. |
| 7,273,469 B1 | 9/2007 | Chan et al. |
| 7,297,475 B2 | 11/2007 | Koiwai et al. |
| 7,326,235 B2 | 2/2008 | Edwards |
| 7,329,236 B2 | 2/2008 | Kesten et al. |
| 7,335,192 B2 | 2/2008 | Keren et al. |
| 7,364,566 B2 | 4/2008 | Elkins et al. |
| 7,373,204 B2 | 5/2008 | Gelfand et al. |
| 7,407,671 B2 | 8/2008 | McBride et al. |
| 7,413,556 B2 | 8/2008 | Zhang et al. |
| 7,444,183 B2 | 10/2008 | Knudson et al. |
| 7,465,298 B2 | 12/2008 | Seward et al. |
| 7,481,803 B2 | 1/2009 | Kesten et al. |
| 7,485,104 B2 | 2/2009 | Kieval |
| 7,507,235 B2 | 3/2009 | Keogh et al. |
| 7,529,589 B2 | 5/2009 | Williams et al. |
| 7,540,870 B2 | 6/2009 | Babaev |
| 7,558,625 B2 | 7/2009 | Levin et al. |
| 7,563,247 B2 | 7/2009 | Maguire et al. |
| 7,599,730 B2 | 10/2009 | Hunter et al. |
| 7,617,005 B2 | 11/2009 | Demarais et al. |
| 7,620,451 B2 | 11/2009 | Demarais et al. |
| 7,640,046 B2 | 12/2009 | Pastore et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,706,882 B2 | 4/2010 | Francischelli et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,766,892 B2 | 8/2010 | Keren et al. |
| 7,837,720 B2 | 11/2010 | Mon |
| 7,905,862 B2 | 3/2011 | Sampson |
| 7,917,208 B2 | 3/2011 | Yomtov et al. |
| 8,016,786 B2 | 9/2011 | Seward et al. |
| 8,027,740 B2 | 9/2011 | Altman et al. |
| 8,119,183 B2 | 2/2012 | O'Donoghue et al. |
| 8,131,371 B2 | 3/2012 | Demarais et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,162,933 B2 | 4/2012 | Francischelli et al. |
| 8,175,711 B2 | 5/2012 | Demarais et al. |
| 8,257,724 B2 | 9/2012 | Cromack et al. |
| 8,257,725 B2 | 9/2012 | Cromack et al. |
| 8,263,104 B2 | 9/2012 | Ho et al. |
| 8,317,776 B2 | 11/2012 | Ferren et al. |
| 8,388,680 B2 | 3/2013 | Starksen et al. |
| 8,396,548 B2 | 3/2013 | Perry et al. |
| 8,399,443 B2 | 3/2013 | Seward |
| 8,403,881 B2 | 3/2013 | Ferren et al. |
| 8,465,752 B2 | 6/2013 | Seward |
| 8,562,573 B1 | 10/2013 | Fischell |
| 8,626,300 B2 | 1/2014 | Demarais et al. |
| 8,663,190 B2 | 3/2014 | Fischell et al. |
| 8,708,995 B2 | 4/2014 | Seward et al. |
| 8,721,590 B2 | 5/2014 | Seward et al. |
| 8,740,849 B1 | 6/2014 | Fischell et al. |
| 8,975,233 B2 | 3/2015 | Stein et al. |
| 9,011,879 B2 | 4/2015 | Seward |
| 9,033,917 B2 | 5/2015 | Magana et al. |
| 9,055,956 B2 | 6/2015 | McRae et al. |
| 9,056,184 B2 | 6/2015 | Stein et al. |
| 9,056,185 B2 | 6/2015 | Fischell et al. |
| 9,108,030 B2 | 8/2015 | Braga |
| 9,114,123 B2 | 8/2015 | Azamian et al. |
| 9,131,983 B2 | 9/2015 | Fischell et al. |
| 9,179,962 B2 | 11/2015 | Fischell et al. |
| 9,199,065 B2 | 12/2015 | Seward |
| 9,237,925 B2 | 1/2016 | Fischell et al. |
| 9,278,196 B2 | 3/2016 | Fischell et al. |
| 9,320,850 B2 | 4/2016 | Fischell et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 2001/0039419 A1 | 11/2001 | Francischelli et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0077592 A1 | 6/2002 | Barry |
| 2002/0082552 A1 | 6/2002 | Ding et al. |
| 2002/0103445 A1 | 8/2002 | Rahdert et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0069619 A1 | 4/2003 | Fenn et al. |
| 2003/0074039 A1 | 4/2003 | Puskas |
| 2003/0082225 A1 | 5/2003 | Mason |
| 2003/0100924 A1 | 5/2003 | Foreman et al. |
| 2003/0114791 A1 | 6/2003 | Rosenthal et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |

(56) References Cited

U.S. PATENT DOCUMENTS

| | | |
|---|---|---|
| 2003/0216792 A1 | 11/2003 | Levin et al. |
| 2003/0220521 A1 | 11/2003 | Reitz et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0043030 A1 | 3/2004 | Griffiths et al. |
| 2004/0062852 A1 | 4/2004 | Schroeder et al. |
| 2004/0064090 A1 | 4/2004 | Keren et al. |
| 2004/0064091 A1 | 4/2004 | Keren et al. |
| 2004/0064093 A1 | 4/2004 | Hektner et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0186468 A1 | 9/2004 | Edwards |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0253304 A1 | 12/2004 | Gross et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0149173 A1 | 7/2005 | Hunter et al. |
| 2005/0149175 A1 | 7/2005 | Hunter et al. |
| 2005/0153885 A1 | 7/2005 | Yun et al. |
| 2005/0154418 A1 | 7/2005 | Kieval et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165467 A1 | 7/2005 | Hunter et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0175661 A1 | 8/2005 | Hunter et al. |
| 2005/0175662 A1 | 8/2005 | Hunter et al. |
| 2005/0177103 A1 | 8/2005 | Hunter et al. |
| 2005/0181004 A1 | 8/2005 | Hunter et al. |
| 2005/0182479 A1 | 8/2005 | Bonsignore et al. |
| 2005/0186242 A1 | 8/2005 | Hunter et al. |
| 2005/0186243 A1 | 8/2005 | Hunter et al. |
| 2005/0187579 A1 | 8/2005 | Danek et al. |
| 2005/0192638 A1 | 9/2005 | Gelfand et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228286 A1 | 10/2005 | Messerly et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0267556 A1 | 12/2005 | Shuros et al. |
| 2005/0282284 A1 | 12/2005 | Rubinsky et al. |
| 2005/0283195 A1 | 12/2005 | Pastore et al. |
| 2006/0004417 A1 | 1/2006 | Rossing et al. |
| 2006/0004430 A1 | 1/2006 | Rossing et al. |
| 2006/0018949 A1 | 1/2006 | Ammon et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100667 A1 | 5/2006 | MacHado et al. |
| 2006/0106429 A1 | 5/2006 | Libbus et al. |
| 2006/0111672 A1 | 5/2006 | Seward |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0240070 A1 | 10/2006 | Cromack et al. |
| 2006/0263393 A1 | 11/2006 | Demopulos et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2006/0280858 A1 | 12/2006 | Kokish |
| 2007/0066957 A1 | 3/2007 | Demarais et al. |
| 2007/0066959 A1 | 3/2007 | Seward |
| 2007/0066972 A1 | 3/2007 | Ormsby et al. |
| 2007/0078620 A1 | 4/2007 | Seward et al. |
| 2007/0083239 A1 | 4/2007 | Demarais et al. |
| 2007/0100318 A1 | 5/2007 | Seward et al. |
| 2007/0106249 A1 | 5/2007 | Seward et al. |
| 2007/0106250 A1 | 5/2007 | Seward et al. |
| 2007/0106251 A1 | 5/2007 | Seward et al. |
| 2007/0106255 A1 | 5/2007 | Seward et al. |
| 2007/0106256 A1 | 5/2007 | Seward et al. |
| 2007/0106257 A1 | 5/2007 | Seward et al. |
| 2007/0118107 A1 | 5/2007 | Francischelli et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0207186 A1 | 9/2007 | Scanlon et al. |
| 2007/0208134 A1 | 9/2007 | Hunter et al. |
| 2007/0208382 A1 | 9/2007 | Yun |

(56) References Cited

U.S. PATENT DOCUMENTS

| | | |
|---|---|---|
| 2007/0219576 A1 | 9/2007 | Cangialosi |
| 2007/0248639 A1 | 10/2007 | Demopulos et al. |
| 2007/0254833 A1 | 11/2007 | Hunter et al. |
| 2007/0265687 A1 | 11/2007 | Deem et al. |
| 2007/0269385 A1 | 11/2007 | Yun et al. |
| 2007/0278103 A1 | 12/2007 | Hoerr et al. |
| 2007/0282376 A1 | 12/2007 | Shuros et al. |
| 2007/0288070 A1 | 12/2007 | Libbus et al. |
| 2007/0299043 A1 | 12/2007 | Hunter et al. |
| 2008/0004596 A1 | 1/2008 | Yun et al. |
| 2008/0004673 A1 | 1/2008 | Rossing et al. |
| 2008/0015659 A1 | 1/2008 | Zhang et al. |
| 2008/0039746 A1 | 2/2008 | Hissong et al. |
| 2008/0039904 A1 | 2/2008 | Bulkes et al. |
| 2008/0045890 A1 | 2/2008 | Seward et al. |
| 2008/0086072 A1 | 4/2008 | Bonutti et al. |
| 2008/0091255 A1 | 4/2008 | Caparso et al. |
| 2008/0140150 A1 | 6/2008 | Zhou et al. |
| 2008/0208162 A1 | 8/2008 | Joshi |
| 2008/0213331 A1 | 9/2008 | Gelfand et al. |
| 2008/0245371 A1 | 10/2008 | Gruber |
| 2008/0255642 A1 | 10/2008 | Zarins et al. |
| 2008/0317818 A1 | 12/2008 | Griffith et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0074828 A1 | 3/2009 | Alexis et al. |
| 2009/0076409 A1 | 3/2009 | Wu et al. |
| 2009/0105631 A1 | 4/2009 | Kieval |
| 2009/0142306 A1 | 6/2009 | Seward et al. |
| 2009/0156988 A1 | 6/2009 | Ferren et al. |
| 2009/0157057 A1 | 6/2009 | Ferren et al. |
| 2009/0216317 A1 | 8/2009 | Cromack et al. |
| 2009/0221955 A1 | 9/2009 | Babaev |
| 2010/0010567 A1 | 1/2010 | Deem et al. |
| 2010/0057150 A1 | 3/2010 | Demarais et al. |
| 2010/0069837 A1 | 3/2010 | Rassat et al. |
| 2010/0087782 A1 | 4/2010 | Ghaffari et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0217162 A1 | 8/2010 | Hissong et al. |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249702 A1 | 9/2010 | Magana et al. |
| 2010/0249773 A1 | 9/2010 | Clark et al. |
| 2010/0268307 A1 | 10/2010 | Demarais et al. |
| 2010/0324472 A1 | 12/2010 | Wulfman |
| 2011/0060324 A1 | 3/2011 | Wu et al. |
| 2011/0104060 A1 | 5/2011 | Seward |
| 2011/0104061 A1 | 5/2011 | Seward |
| 2011/0112400 A1 | 5/2011 | Emery et al. |
| 2011/0137155 A1 | 6/2011 | Weber et al. |
| 2011/0137298 A1 | 6/2011 | Nguyen et al. |
| 2011/0178570 A1 | 7/2011 | Demarais |
| 2011/0182912 A1 | 7/2011 | Evans et al. |
| 2011/0184337 A1 | 7/2011 | Evans et al. |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0257622 A1 | 10/2011 | Salahieh et al. |
| 2011/0264011 A1 | 10/2011 | Wu et al. |
| 2011/0264075 A1 | 10/2011 | Leung et al. |
| 2012/0172837 A1 | 7/2012 | Demarais et al. |
| 2012/0259269 A1 | 10/2012 | Meyer |
| 2012/0271277 A1 | 10/2012 | Fischell et al. |
| 2012/0271301 A1 | 10/2012 | Fischell et al. |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0096604 A1 | 4/2013 | Hanson et al. |
| 2013/0172815 A1 | 7/2013 | Perry et al. |
| 2013/0204131 A1 | 8/2013 | Seward |
| 2013/0252932 A1 | 9/2013 | Seward |
| 2013/0274673 A1 | 10/2013 | Fischell et al. |
| 2013/0274674 A1 | 10/2013 | Fischell et al. |
| 2013/0287698 A1 | 10/2013 | Seward |
| 2013/0296853 A1 | 11/2013 | Sugimoto et al. |
| 2014/0012231 A1 | 1/2014 | Fischell |
| 2014/0046298 A1 | 2/2014 | Fischell et al. |
| 2014/0107478 A1 | 4/2014 | Seward et al. |
| 2014/0121641 A1 | 5/2014 | Fischell et al. |
| 2014/0121644 A1 | 5/2014 | Fischell et al. |
| 2014/0135661 A1 | 5/2014 | Garrison et al. |
| 2014/0236103 A1 | 8/2014 | Fischell et al. |
| 2014/0271717 A1 | 9/2014 | Goshayeshgar et al. |
| 2014/0276621 A1 | 9/2014 | Braga |
| 2014/0296279 A1 | 10/2014 | Seward et al. |
| 2014/0303569 A1 | 10/2014 | Seward et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0132409 A1 | 5/2015 | Stein et al. |
| 2015/0202220 A1 | 7/2015 | Stein et al. |
| 2015/0224289 A1 | 8/2015 | Seward |
| 2015/0231386 A1 | 8/2015 | Meyer |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2015/0343175 A1 | 12/2015 | Braga |
| 2016/0008387 A9 | 1/2016 | Stein et al. |
| 2016/0051465 A1 | 2/2016 | Azamian et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0310200 A1 | 10/2016 | Wang |
| 2016/0354137 A1 | 12/2016 | Fischell et al. |

FOREIGN PATENT DOCUMENTS

| | | |
|---|---|---|
| DE | 3151180 | 8/1982 |
| EP | 0233100 | 8/1987 |
| EP | 0497041 | 8/1992 |
| EP | 0774991 | 5/1997 |
| EP | 0811395 | 12/1997 |
| EP | 1782852 | 5/2007 |
| EP | 2092957 | 8/2009 |
| EP | 2352542 | 8/2011 |
| EP | 2429641 | 3/2012 |
| EP | 2528649 | 12/2012 |
| EP | 2656807 | 10/2013 |
| EP | 2675458 | 12/2013 |
| EP | 2694150 | 2/2014 |
| EP | 2747688 | 7/2014 |
| EP | 2885041 A1 | 6/2015 |
| EP | 2911735 A1 | 9/2015 |
| EP | 2914326 A2 | 9/2015 |
| EP | 3060148 A1 | 8/2016 |
| EP | 3132828 A1 | 2/2017 |
| EP | 3158866 | 4/2017 |
| JP | 49009882 | 1/1974 |
| JP | 6218122 | 8/1987 |
| JP | 3041967 | 10/1997 |
| JP | 2003510126 | 3/2003 |
| JP | 2004016333 | 1/2004 |
| WO | WO-85/01213 | 3/1985 |
| WO | WO-91/04725 | 4/1991 |
| WO | WO-9220291 | 11/1992 |
| WO | WO-93/02740 | 2/1993 |
| WO | WO-93/07803 | 4/1993 |
| WO | WO-94/00188 | 1/1994 |
| WO | WO-1994007446 | 4/1994 |
| WO | WO-94/11057 | 5/1994 |
| WO | WO-95/25472 | 9/1995 |
| WO | WO-1995031142 | 11/1995 |
| WO | WO-95/33514 | 12/1995 |
| WO | WO-96/00039 | 1/1996 |

(56) References Cited

FOREIGN PATENT DOCUMENTS

| | | |
|---|---|---|
| WO | WO-96/04957 | 2/1996 |
| WO | WO-96/11723 | 4/1996 |
| WO | WO-1997003604 | 2/1997 |
| WO | WO-97/13463 | 4/1997 |
| WO | WO-97/13550 | 4/1997 |
| WO | WO-1997036548 | 10/1997 |
| WO | WO-97/42990 | 11/1997 |
| WO | WO-97/49453 | 12/1997 |
| WO | WO-98/37926 | 9/1998 |
| WO | WO-98/42403 | 10/1998 |
| WO | WO-98/43700 | 10/1998 |
| WO | WO-98/43701 | 10/1998 |
| WO | WO-1998042403 | 10/1998 |
| WO | WO-98/48888 | 11/1998 |
| WO | WO-1999000060 | 1/1999 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-2001022897 | 4/2001 |
| WO | WO-0170114 | 9/2001 |
| WO | WO-02/09808 | 2/2002 |
| WO | WO-02/26314 | 4/2002 |
| WO | WO-02/053207 | 7/2002 |
| WO | WO-2002058549 | 8/2002 |
| WO | WO-02/070039 | 9/2002 |
| WO | WO-02/070047 | 9/2002 |
| WO | WO-02/085448 | 10/2002 |
| WO | WO-2002085192 | 10/2002 |
| WO | WO-03/018108 | 3/2003 |
| WO | WO-03024311 | 3/2003 |
| WO | WO-2003022167 | 3/2003 |
| WO | WO-03/028802 | 4/2003 |
| WO | WO-03/063692 | 8/2003 |
| WO | WO-03/071140 | 8/2003 |
| WO | WO-03/076008 | 9/2003 |
| WO | WO-03/082403 | 10/2003 |
| WO | WO-2003/082080 | 10/2003 |
| WO | WO-2004/011055 | 2/2004 |
| WO | WO-2004/026370 | 4/2004 |
| WO | WO-2004/026371 | 4/2004 |
| WO | WO-2004/026374 | 4/2004 |
| WO | WO-2004/028583 | 4/2004 |
| WO | WO-2004/030718 | 4/2004 |
| WO | WO-2004/032791 | 4/2004 |
| WO | WO-2004049976 | 6/2004 |
| WO | WO-2004/107965 | 12/2004 |
| WO | WO-2005/007000 | 1/2005 |
| WO | WO-2005/014100 | 2/2005 |
| WO | WO-2005/016165 | 2/2005 |
| WO | WO-05/032646 | 4/2005 |
| WO | WO-2005/032646 | 4/2005 |
| WO | WO-2005030072 | 4/2005 |
| WO | WO-2005041748 | 5/2005 |
| WO | WO-2005/065284 | 7/2005 |
| WO | WO-2005/084389 | 9/2005 |
| WO | WO-2005/097256 | 10/2005 |
| WO | WO-2005/110528 | 11/2005 |
| WO | WO-2005/123183 | 12/2005 |
| WO | WO-2006/007048 | 1/2006 |
| WO | WO-2006/018528 | 2/2006 |
| WO | WO-2006/022790 | 3/2006 |
| WO | WO-2006/031899 | 3/2006 |
| WO | WO-2006041847 | 4/2006 |
| WO | WO-2006041881 | 4/2006 |
| WO | WO-2007008954 | 1/2007 |
| WO | WO-2007035537 | 3/2007 |
| WO | WO-2007078997 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008049084 | 4/2008 |
| WO | WO-2008061150 | 5/2008 |
| WO | WO-2008061152 | 5/2008 |
| WO | WO-2008070413 | 6/2008 |
| WO | WO-2009088678 | 7/2009 |
| WO | WO-2010042653 | 4/2010 |
| WO | WO-2010078175 | 7/2010 |
| WO | WO-2011094367 | 8/2011 |
| WO | WO-2011133724 | 10/2011 |
| WO | WO-2012161875 | 11/2012 |
| WO | WO-2013028781 | 2/2013 |
| WO | WO-2013059735 | 4/2013 |
| WO | WO-2013063331 | 5/2013 |
| WO | WO-2013112844 | 8/2013 |
| WO | WO-2013169741 | 11/2013 |
| WO | WO-2013188689 | 12/2013 |
| WO | WO-2014031167 | 2/2014 |
| WO | WO-2014070820 | 5/2014 |
| WO | WO-2014070999 | 5/2014 |
| WO | WO-2014078301 | 5/2014 |
| WO | WO-2014189887 | 11/2014 |

OTHER PUBLICATIONS

Opposition to European Patent No. 2465470, Granted Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2

(56) References Cited

OTHER PUBLICATIONS pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Intery Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages,

(56) References Cited

OTHER PUBLICATIONS

<http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.

Bello-Reuss, E. et al., Effects of Acute Unilateral Renal Denervation in the Rat, J Clin Invest, 1975, 56: 10 pgs.
Gonschior, P., Comparison of Local Intravascular Drug-Delivery Catheter Systems, Am. Heart J., Dec. 1995, 130:6, 1174-81.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter, "Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278.00.html.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 60/813,589, filed Dec. 29, 2005, Demarais et al.
2003 European Society of Hypertension—European Society of Cardiology guidelines for the management of arterial hypertension, Guidelines Committee, Journal of Hypertension 2003, vol. 21, No. 6, pp. 1011-1053.

(56) References Cited

OTHER PUBLICATIONS

Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.

Abramov, G.S. et al., Alteration in sensory nerve function following electrical shock, Burns vol. 22, No. 8, 1996 Elsevier Science Ltd., pp. 602-606.

Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.

Advanced Neuromodulation Systems' Comparison Chart, Dec. 16, 2008, pp. 1.

Advances in the role of the sympathetic nervous system in cardiovascular medicine, 2001 SNS Report, No. 3, Springer, Published with an educational grant from Servier, pp. 1-8.

Aggarwal, A. et al., Regional sympathetic effects of low-dose clonidine in heart failure. Hypertension. 2003;41:553-7.

Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.

Ahadian, Farshad M., M.D., Pulsed Radiofrequency Neurotomy: Advances in Pain Medicine, Current Pain and Headache Reports 2004, vol. 8, 2004 Current Science Inc., pp. 34-40.

Alexander, B.T. et al., Renal denervation abolishes hypertension in low-birth-weight offspring from pregnant rats with reduced uterine perfusion, Hypertension, 2005; 45 (part 2): pp. 754-758.

Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.

Allen, E.V., Sympathectomy for essential hypertension, Circulation, 1952, 6:131-140.

Amersham Health. Hypaque-Cysto, 2003, 6 pages.

Andrews, B.T. et al., The use of surgical sympathectomy in the treatment of chronic renal pain. Br J Urol. 1997; 80: 6-10.

Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.

Archer, Steffen et al., Cell Reactions to Dielectrophoretic Manipulation, Mar. 1, 1999, Biochemical and Biophysical Research Communications, 1999 Academic Press, pp. 687-698.

Arentz, T. et al., Incidence of pulmonary vein stenosis 2 years after radiofrequency catheter ablation of refractory atrial fibrillation. European Heart Journal. 2003. 24; pp. 963-969.

Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.

Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.

Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.

Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.

Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.

Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.

Badyal, D. K., H. Lata and A.P. Dadhich, Animal Models of Hypertension and Effect of Drugs, Aug. 19, 2003, Indian Journal of Pharmacology 2003, vol. 35, pp. 349-362.

Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.

Balazs, Tibor, Development of Tissue Resistance to Toxic Effects of Chemicals, Jan. 26, 1974, Toxicology, 2 (1974), Elsevier/North-Holland, Amsterdam, pp. 247-255.

Barajas, L. Innervation of the renal cortex. Fex Proc. 1978;37:1192-201.

Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.

Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.

Bassett, C. Andrew L. et al., Augmentation of Bone Repair by Inductively Coupled Electromagnetic Fields, May 3, 1974, Science, vol. 184, pp. 575-577.

Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.

Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.

Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.

Bello-Reuss, E. et al., Acute unilateral renal denervation in rats with extracellular volume expansion, Departments of Medicine and Physiology, University of North Carolina School of Medicine. F26-F32 Jul. 1975.

Bello-Reuss, E. et al., Effect of renal sympathetic nerve stimulation on proximal water and sodium reabsorption, J Clin Invest, 1976;57:1104-1107.

Bello-Reuss, E. et al., Effects of Acute Unilateral Renal Denervation in the Rat, J Clin Invest, 1975;56:208-217.

Berde, C. et al., Local Anesthetics, Anesthesia, Chapter 13, 5th addition, Churchill-Livingston, Philadelphia 2000, pp. 491-521.

Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.

Bhandari, A. and Ellias, M., Loin pain hematuria syndrome: Pain control with RFA to the Splanchanic plexus, The Pain Clinic, 2000, vol. 12, No. 4, pp. 323-327.

Bhatt, Deepak L. et al., Rhabdomyolysis Due to Pulsed Electric Fields, May 11, 1989, Plastic and Reconstructive Surgery Jul. 1990, pp. 1-11.

Bichet, D., et al., Renal intracortical blood flow and renin secretion after denervation by 6-hydroxydopamine. Can J Physiol Pharmacol. 1982;60:184-92.

Bigler, D. et al., Tachyphylaxis during postoperative epidural analgesia—new insights, Apr. 15, 1987, Letter to the Editor, Acta Anaesthesiol Scand. 1987, vol. 31, pp. 664-665.

Binder, Allan et al., Pulsed Electromagnetic Field Therapy of Persistent Rotator Cuff Tendinitis, The Lancet, Saturday Mar. 31, 1984, The Lancet Ltd., pp. 695-698.

Black, M.D., Henry R., Resistant Hypertension 2004, presentation at Rush University Medical Center, Jul. 15, 2004, 40 pages.

(56) References Cited

OTHER PUBLICATIONS

Blad, B., et al., An Electrical Impedance index to Assess Electroporation in Tissue, Tissue and Organ (Therapy), 2001, Oslo, www.bl.uk <http://www.bl.uk> British Library, pp. 31-34.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.
Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.

Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005, 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical theray for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.

(56) References Cited

OTHER PUBLICATIONS

Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.
Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.
DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
Dibona, Gerald F., Sympathetic Nervous System and the Kidney in Hypertension, Current Opinion in Nephrology and Hypertension 2002, vol. 11, 2002 Lippincott Williams & Wilkins, pp. 197-200.
Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.

Dibona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; dated Jan. 19, 2010, 4 pgs.
European Examination Report; European Patent Application No. 09156661.2; Applicant: Ardian, Inc.; dated Jan. 19, 2010, 6 pgs.
European Search Report; European Patent Application No. 05806045.0; Applicant: Ardian, Inc.; dated Jan. 22, 2009, 8 pgs.
European Search Report; European Patent Application No. 05811851.4; Applicant: Ardian, Inc.; dated Oct. 1, 2009, 7 pgs.
European Search Report; European Patent Application No. 06847926.0; Applicant: Ardian, Inc.; dated Feb. 10, 2010, 6 pgs.
European Search Report; European Patent Application No. 07757925.8; Applicant: Ardian, Inc.; dated Apr. 29, 2010, 9 pgs.
European Search Report; European Patent Application No. 07798341.9; Applicant: Ardian, Inc.; dated Aug. 4, 2011; 6 pgs.
European Search Report; European Patent Application No. 07799148.7; Applicant: Ardian, Inc.; dated Jul. 23, 2009, 6 pgs.
European Search Report; European Patent Application No. 07868755.5; Applicant: Ardian, Inc.; dated Jul. 28, 2010, 7 pgs.
European Search Report; European Patent Application No. 09156661.2; Applicant: Ardian, Inc.; dated Jul. 23, 2009, 6 pgs.

(56) References Cited

OTHER PUBLICATIONS

European Search Report; European Patent Application No. 09167937.3; Applicant: Ardian, Inc.; dated Nov. 11, 2009, 6 pgs.
European Search Report; European Patent Application No. 09168202.1; Applicant: Ardian, Inc.; dated Nov. 11, 2009, 5 pgs.
European Search Report; European Patent Application No. 09168204.7; Applicant: Ardian, Inc.; dated Nov. 19, 2009, 6 pgs.
Evelyn, K.A. et al., Effect of thoracolumbar sympathectomy on the clinical course of primary (essential) hypertension, Am J Med, 1960;28:188-221.
Ex parte Quayle Office Action; U.S. Appl. No. 11/144,173; dated May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; dated Jan. 29, 2009, 11 pgs.
Final Office Action; U.S. Appl. No. 11/266,993; dated Jan. 8, 2010, 7 pgs.
Final Office Action; U.S. Appl. No. 11/363,867; dated May 1, 2009, 8 pgs.
Final Office Action; U.S. Appl. No. 11/451,728; dated Jan. 13, 2009, 7 pgs.
Final Office Action; U.S. Appl. No. 11/599,649; dated Jan. 15, 2009, 10 pgs.
Final Office Action; U.S. Appl. No. 11/599,723; dated Apr. 5, 2010, 17 pgs.
Final Office Action; U.S. Appl. No. 11/599,890; dated Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.

Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.
Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to Tens in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.

(56) References Cited

OTHER PUBLICATIONS

Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104 (4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.
Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.
Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, by Gender, B.C., 2001/2002, Graph, Chronic Disease Management, May 2003, British Columbia Ministry of Health Services, 1 page.
Implantable Neurostimulation Systems, Medtronic Neurological, Jan. 18, 1999, 6 pages. http://medtronic.com/neuro/paintherapies/pain_treatment_ladder/pdf/implantable_brochure.pdf.
Implantable Pump—The Medtronic MiniMed 2007 Implantable Insulin Pump System, Medtronic MiniMed 2004, 4 pgs.
International Search Report and Written Opinion for PCT/US2009/069334; Applicant: Ardian, Inc.; dated Mar. 1, 2010, 10 pgs.
International Search Report and Written Opinion, PCT/US05/35693, dated Mar. 8, 2006, Applicant: Ardian, Inc., 29 pgs.
International Search Report and Written Opinion, PCT/US05/35757, dated Dec. 27, 2006, Applicant: Ardian, Inc., 8 pgs.
International Search Report and Written Opinion, PCT/US06/36120, dated Jun. 25, 2008, Applicant: Ardian, Inc., 10 pgs.
International Search Report and Written Opinion, PCT/US06/41889, dated Oct. 20, 2008, Applicant: Ardian, Inc., 7 pgs.
International Search Report and Written Opinion, PCT/US06/48822, dated Aug. 15, 2008, Applicant: Ardian, Inc., 12 pgs.
International Search Report and Written Opinion, PCT/US07/63322, dated Mar. 3, 2008, Applicant: Ardian, Inc., 13 pgs.
International Search Report and Written Opinion, PCT/US07/63324, dated Oct. 10, 2008, Applicant: Ardian, Inc., 10 pgs.
International Search Report and Written Opinion, PCT/US07/66539, dated Jan. 28, 2008, Applicant: Ardian, Inc., 6 pgs.
International Search Report and Written Opinion, PCT/US07/70799, dated Jul. 2, 2008, Applicant: Ardian, Inc., 7 pgs.
International Search Report and Written Opinion, PCT/US07/72396, dated Aug. 27, 2008, Applicant: Ardian, Inc., 9 pgs.
International Search Report and Written Opinion, PCT/US07/84701, dated Aug. 21, 2008, Applicant: Ardian, Inc., 11 pgs.
International Search Report and Written Opinion, PCT/US07/84705, dated Jul. 28, 2008, Applicant: Ardian, Inc., 12 pgs.
International Search Report and Written Opinion, PCT/US07/84708, dated Aug. 11, 2008, Applicant: Ardian, Inc., 9 pgs.
International Search Report, PCT/US02/0039, dated Sep. 11, 2002, Applicant: Advanced Neuromodulation Systems, Inc.
International Search Report, PCT/US02/25712, dated Apr. 23, 2003, Applicant: Cyberonics, Inc.
International Search Report, PCT/US03/08014, dated Sep. 23, 2003, Applicant: The General Hospital Corporation.
International Search Report, PCT/US03/09764, dated Oct. 28, 2003, Applicant: CVRX, Inc.
International Search Report, PCT/US04/38498, dated Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.

(56) References Cited

OTHER PUBLICATIONS

Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Joye, James D.et al., In Vivo Study of Endovascular Cryotherapy for the Prevention of Restenosis, 4 pages, 2003.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II): II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha 1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.

Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, Sleep 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.
Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee, Raphael C. et al., Membrane Biology and Biophysics, Chapter 25, Surgical Research, 2001 Academic Press, pp. 297-305.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.
Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.
Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ struc-

(56) References Cited

OTHER PUBLICATIONS turally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.
Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited Review, Am J Physiol Regul lntegr Comp Physiol 2004, vol. 286, 2004 the American Physiological Society, pp. R1-R12.
Mancia, G., Grassi, G., Giannattasio, C., Seravalle, G., Sympathetic activation of pathogenesis of hypertension and progression of organ damage, Hypertension 1999, 34 (4 Pt 2): 724-728.
Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
McCullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.
McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
McRobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis USA Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCI) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You at Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; dated Mar. 21, 2006, 14 pgs.
Non-Final Office Action; U.S. Appl. No. 11/129,765; date May 18, 2007, 10 pgs.
Non-Final Office Action; U.S. Appl. No. 11/129,765; dated Sep. 10, 2007, 5 pgs.
Non-Final Office Action; U.S. Appl. No. 11/129,765; dated Oct. 6, 2006, 30 pgs.
Non-Final Office Action; U.S. Appl. No. 11/133,925; dated Oct. 8, 2008, 41 pgs.
Non-Final Office Action; U.S. Appl. No. 11/144,173; dated Apr. 5, 2007, 33 pgs.
Non-Final Office Action; U.S. Appl. No. 11/144,173; dated Sep. 10, 2007, 5 pgs.
Non-Final Office Action; U.S. Appl. No. 11/144,298; dated Oct. 29, 2009, 8 pgs.
Non-Final Office Action; U.S. Appl. No. 11/144,298; dated Apr. 5, 2007, 33 pgs.
Non-Final Office Action; U.S. Appl. No. 11/144,298; dated Sep. 10, 2007, 5 pgs.
Non-Final Office Action; U.S. Appl. No. 11/144,298; dated Dec. 29, 2008, 7 pgs.
Non-Final Office Action; U.S. Appl. No. 11/145,122; dated Apr. 11, 2007, 33 pgs.
Non-Final Office Action; U.S. Appl. No. 11/145,122; dated Sep. 10, 2007, 5 pgs.
Non-Final Office Action; U.S. Appl. No. 11/189,563; dated May 28, 2009, 5 pgs.
Non-Final Office Action; U.S. Appl. No. 11/233,814; dated Jun. 17, 2008, 12 pgs.
Non-Final Office Action; U.S. Appl. No. 11/252,462; dated Feb. 22, 2010, 6 pgs.
Non-Final Office Action; U.S. Appl. No. 11/266,993; dated Jul. 8, 2009, 5 pgs.
Non-Final Office Action; U.S. Appl. No. 11/266,993; dated Dec. 30, 2008, 7 pgs.
Non-Final Office Action; U.S. Appl. No. 11/363,867; dated Sep. 25, 2008, 10 pgs.
Non-Final Office Action; U.S. Appl. No. 11/368,553; dated May 18, 2010, 4 pgs.
Non-Final Office Action; U.S. Appl. No. 11/368,553; dated Oct. 7, 2009, 5 pgs.
Non-Final Office Action; U.S. Appl. No. 11/368,809; dated Dec. 3, 2009, 4 pgs.

(56) References Cited

OTHER PUBLICATIONS

Non-Final Office Action; U.S. Appl. No. 11/368,949; dated Jun. 11, 2010, 6 pgs.
Non-Final Office Action; U.S. Appl. No. 11/368,971; dated Aug. 24, 2010, 9 pgs.
Non-Final Office Action; U.S. Appl. No. 11/451,728; dated Jun. 12, 2008, 41 pgs.
Non-Final Office Action; U.S. Appl. No. 11/451,728; dated Jul. 2, 2009, 5 pgs.
Non-Final Office Action; U.S. Appl. No. 11/451,728; dated Dec. 28, 2009, 7 pgs.
Non-Final Office Action; U.S. Appl. No. 11/504,117; dated Mar. 31, 2009, 10 pgs.
Non-Final Office Action; U.S. Appl. No. 11/599,649; dated Mar. 30, 2009, 10 pgs.
Non-Final Office Action; U.S. Appl. No. 11/599,649; dated Jun. 23, 2008, 9 pgs.
Non-Final Office Action; U.S. Appl. No. 11/599,723; dated Jun. 26, 2009, 17 pgs.
Non-Final Office Action; U.S. Appl. No. 11/599,723; dated Oct. 15, 2010, 16 pgs.
Non-Final Office Action; U.S. Appl. No. 11/599,882; dated Jul. 6, 2009, 13 pgs.
Non-Final Office Action; U.S. Appl. No. 11/688,178; dated Jun. 28, 2010, 5 pgs.
Non-Final Office Action; U.S. Appl. No. 11/840,142; dated Apr. 3, 2009, 13 pgs.
Non-Final Office Action; U.S. Appl. No. 12/567,521; dated Sep. 3, 2010, 9 pgs.
Non-Final Office Action; U.S. Appl. No. 12/616,708; dated Sep. 16, 2010, 10 pgs.
Non-Final Office Action; U.S. Appl. No. 12/725,375; dated Oct. 12, 2010, 14 pgs.
Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, Spine, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Tri-

(56) References Cited

OTHER PUBLICATIONS als, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . An Implantable Bolus Infusion Pump for the Neurosciences, FRP, Apr. 2005, 3 pages.

Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006).
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.
Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.

(56) References Cited

OTHER PUBLICATIONS

Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.

Steffen, W. et al., Catheter-delivered high intensity, low frequency ultrasound induces vasodilation in vivo, European Heart Journal. 1994. 15; pp. 369-376.

Steg, PG et al., Pulsed ultraviolet laser irradiation produces endothelium-independent relaxation of vascular smooth muscle, Circulation: Journal of the American Heart Association. 1989. pp. 189-197.

Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

Strojek, K. et al., Lowering of microalbuminuria in diabetic patients by a sympathicoplegic agent: novel approach to prevent progression of diabetic nephropathy? J Am Soc Nephrol. 2001;12:602-5.

Summary, Critical Reviews in Biomedical Engineering, vol. 17, Issue 5, 1989, pp. 515-529.

Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.

Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.

Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.

Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.

Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.

Terashima, Mitsuyasu et al. Feasibility and Safety of a Novel CryoPlasty™ System. Poster. 1 page, Mar. 15, 2002.

Thatipelli et al., CT Angiography of Renal Artery Anatomy for Evaluating Embolic Protection Devices, Journal of Vascular and Interventional Radiology, Jul. 2007, pp. 842-846.

The Antihypertensive and Lipid-Lowering Treatment to Prevent Heart Attack Trial, ALLHAT Research Group, JAMA, 2002, vol. 288, pp. 2981-2997.

Thomas, John R. and Oakley, E. Howard N. Chapter 15: Nonfreezing Cold Injury Medical Aspects of Harsh Environments, vol. 1. pp. 467-490, 2001.

Thompson, Gregory W., et al., Bradycardia Induced by Intravascular Versus Direct Stimulation of the Vagus Nerve, Aug. 24, 1997, The Society of Thoracic Surgeons 1998, pp. 637-642.

Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.

Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.

Trapani, Angelo J. et al., Neurohumoral interactions in conscious dehydrated rabbit, Am. J. Physiol. 254, 1988, the American Physiological Society 1988, pp. R338-R347.

Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.

Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.

Trumble, Dennis R. and James A. MaGovern, Comparison of Dog and Pig Models for Testing Substernal Cardiac Compression Devices, Nov. 2003, ASAIO Journal 2004, pp. 188-192.

Tsai, E., Intrathecal drug delivery for pain indications, technique, results, Pain Lecture presentation, Jun. 8, 2001, 31 pages.

Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.

Valente, John F. et al., Laparoscopic renal denervation for intractable ADPKD-related pain, Aug. 24, 2000, Nephrol Dial Transplant 2001, vol. 16, European Renal Association—European Dialysis and Transplant Association, p. 160.

Van Antwerp, Bill and Poonam Gulati, Protein Delivery from Mechanical Devices Challenges and Opportunities, Medtronic presentation, 19 pages, Jul. 2003.

Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.

Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.

Villarreal, Daniel et al., Effects of renal denervation on postprandial sodium excretion in experimental heart failure, Oct. 29, 1993, Am J Physiol 266, 1994, pp. R1599-R1604.

Villarreal, Daniel et al., Neurohumoral modulators and sodium balance in experimental heart failure, Nov. 6, 1992, Am. J. Physiol, vol. 264, 1993, pp. H1187-H1193.

Vonend, O. et al., Moxonidine treatment of hypertensive patients with advanced renal failure. J Hypertens. 2003;21:1709-17.

Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.

Wald, Jan D., Ph.D, et al., Cardiology Update: 2003, Sep. 11, 2003, AG Edwards 2003, 120 pages.

Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.

Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.

Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.

Weiner, Richard L., M.D., Peripheral nerve neurostimulation, Neurosurg. Clin. N. Am. vol. 14, 2003, Elsevier, Inc. 2003, pp. 401-408.

Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.

Whitelaw, G.P., Kinsey, D., Smithwick, R.H., Factors influencing the choice of treatment in essential hypertension: surgical, medical, or a combination of both, Am J Surg, 1964, 107:220-231.

(56) References Cited

OTHER PUBLICATIONS

Wilson, D.H. et al., The Effects of Pulsed Electromagnetic Energy on Peripheral Nerve Regeneration, Annals New York Academy of Sciences, Oct. 1974, pp. 575-585.

Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.

Wyss, J. Michael et al., Neuronal control of the kidney: Contribution to hypertension, Apr. 8, 1991, Can. J. Physiol. Pharmacol. 1992;70: 759-770.

Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.

Ye, Richard D., M.D., Ph.D., Pharmacology of the Peripheral Nervous System, E-425 MSB, 6 pages, Jan. 2000.

Ye, S. et al., A limited renal injury may cause a permanent form of neurogenic hypertension. Am J Hypertens. 1998;11:723-8.

Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.

Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.

Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.

Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.

Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.

Zanchetti, A. et al., Practice Guidelines for Primary Care Physicians: 2003 ESH/ESC Hypertension Guidelines, Journal of Hypertension, vol. 21, No. 10, 2003, pp. 1779-1786.

Zanchetti, A.S., Neural regulation of renin release: Experimental evidence and clinical implications in arterial hypertension, Circulation, 1977, 56(5) 691-698.

Zimmermann, Ulrich, Electrical Breakdown, Electropermeabilization and Electrofusion, Rev. Physiol. Biochem. Pharmacol., vol. 105, Springer-Verlag 1986, pp. 175-256.

Zoccali, C. et al., Plasma norepinephrine predicts survival and incident cardiovascular events in patients with end-stage renal disease. Circulation. 2002;105:1354-9.

Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

Zundert, Jan Van, M.D. Fipp and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.

\* cited by examiner

METHODS AND APPARATUS FOR THERMALLY-INDUCED RENAL NEUROMODULATION

REFERENCE TO RELATED APPLICATIONS

The present application is a continuation of U.S. patent application Ser. No. 14/094,330, filed Dec. 2, 2013, which is a continuation of U.S. patent application Ser. No. 13/046, 595, now U.S. Pat. No. 8,626,300, which is a continuation of U.S. patent application Ser. No. 11/599,723, filed Nov. 14, 2006, now abandoned, which claims the benefit of U.S. Provisional Application No. 60/816,999filed on Jun. 28, 2006. U.S. patent application Ser. No. 11/599,723, filed Nov. 14, 2006, is also a continuation-in-part application of U.S. patent application Ser. No. 10/408,665, now U.S. Pat. No. 7,162,303, which claims the benefit of U.S. Provisional Application Nos. (a) 60/370,190, filed on Apr. 8, 2002, (b) 60/415,575, filed on Oct. 3, 2002, and (c) 60/442,970, filed on Jan. 29, 2003. Furthermore, U.S. patent application Ser. No. 11/599,723, filed Nov. 14, 2006, is a continuation-in-part application of U.S. patent application Ser. No. 11/189, 563, now U.S. Pat. No. 8,145,316, which is a continuation-in-part application of U.S. patent application Ser. No. 11/129,765, filed on May. 13, 2005, now U.S. Pat. No. 7,653,438, and which claims the benefit of U.S. Provisional Application Nos. (a) 60/616,254, filed on Oct. 5, 2004, and (b) 60/624,793, filed on Nov. 2, 2004. Further still, U.S. patent application Ser. No. 11/599,723, filed Nov. 14, 2006, is a continuation-in-part application of U.S. patent application Ser. No. 11/504,117, now U.S. Pat. No. 7,617,005.

All of these applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. More particularly, the present invention relates to methods and apparatus for achieving renal neuromodulation via thermal heating and/or cooling mechanisms.

BACKGROUND

Heart Failure or Chronic Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Renal Failure or Chronic Renal Failure ("CRF"), Renal Disease or End-Stage Renal Disease ("ESRD"), Hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys, which causes decreased renal blood flow. Reduction of sympathetic renal nerve activity, e.g., via denervation, may reverse these processes.

Applicants have described methods and apparatus for treating renal disorders by applying a pulsed electric field, preferably non-thermal, to neural fibers that contribute to renal function. See, for example, Applicants' co-pending U.S. patent application Ser. Nos. (a) 11/129,765, filed on May. 13, 2005, (b) 11/189,563, filed on Jul. 25, 2005, and (c) 11/363,867, filed Feb. 27, 2006, all of which are incorporated herein by reference in their entireties. A pulsed electric field ("PEF") may initiate renal denervation or other neuromodulation via irreversible electroporation or other processes. The PEF may be delivered from apparatus positioned intravascularly, extravascularly, intra-to-extravascularly or a combination thereof. Additional methods and apparatus for achieving renal neuromodulation via localized drug delivery (such as by a drug pump or infusion catheter) or use of a stimulation electric field are described in co-owned and co-pending U.S. patent application Ser. No. 10/408,665, filed Apr. 8, 2003, and U.S. Pat. No. 6,978,174, both of which are incorporated herein by reference in their entireties.

A potential challenge of using non-thermal PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of non-thermal PEF therapy may persistently injure the renal vasculature, but an overly conservative course of non-thermal PEF therapy may not achieve the desired renal neuromodulation.

Applicants have previously described methods and apparatus for monitoring changes in tissue impedance or conductivity in order to determine the effects of pulsed electric field therapy. Such changes in tissue can be used to determine an extent of electroporation and/or its degree of irreversibility in target or non-target tissue. See, for example, Applicant's co-pending U.S. patent application Ser. No. 11/233,814, filed Sep. 23, 2005, which is incorporated herein by reference in its entirety. However, in some patients it may be difficult or impractical to achieve such real-time monitoring when utilizing non-thermal pulsed electric field neuromodulatory mechanisms. In some patients, this may necessitate re-intervention the degree of induced neuromodulation was not sufficient to achieve a desired treatment outcome. Conversely, an overly aggressive course of relatively unmonitored or uncontrolled therapy may induce undesirable and/or persistent damage in non-target tissue. Thus, it would be desirable to achieve renal neuromodulation via more easily monitored and/or controlled neuromodulatory mechanisms.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

Figure 1:
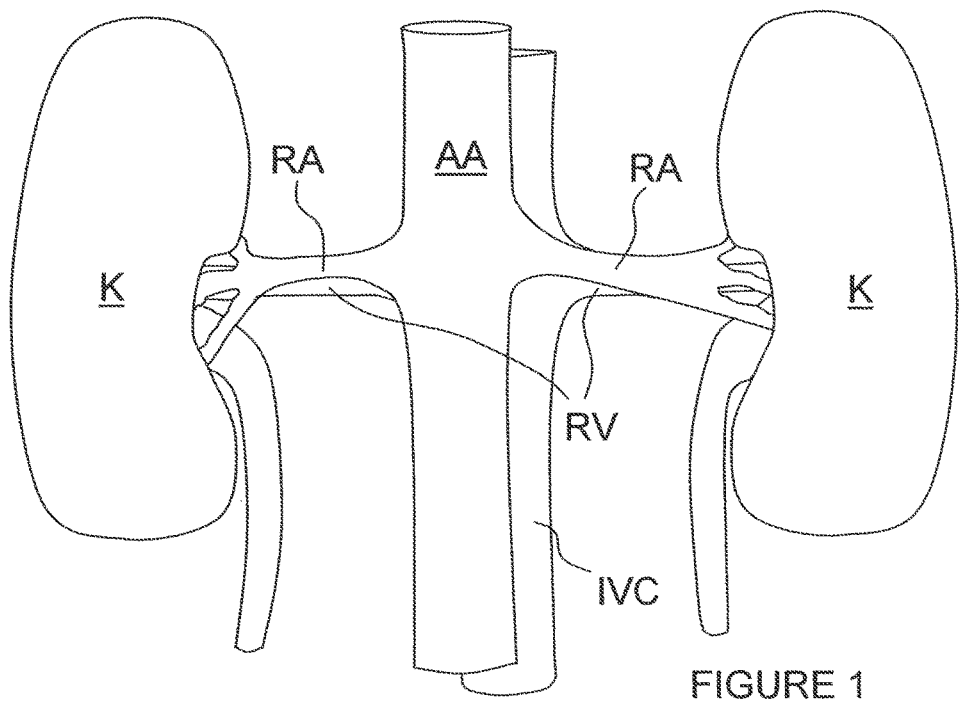
FIG. 1 is a schematic view illustrating human renal anatomy.

The following describes several embodiments of methods and apparatus for renal neuromodulation via thermal heating and/or thermal cooling mechanisms. Many embodiments of such methods and apparatus may reduce renal sympathetic nerve activity. Thermally-induced (via heating and/or cooling) neuromodulation may be achieved via apparatus positioned proximate target neural fibers, such as being positioned (a) within renal vasculature (i.e., positioned intravascularly), (b) extravascularly, (c) intra-to-extravascularly, or (d) a combination thereof. Thermal neuromodulation by heating or cooling may be caused by directly effecting or otherwise altering the neural structures that are subject to the thermal stress. Additionally or alternatively, the thermal neuromodulation may at least in part be due to alteration of arteries, arterioles, capillaries, or veins or other vascular structures which perfuse the target neural fibers or surrounding tissue. Furtherstill, the modulation may at least in part be caused by electroporation of the target neural fibers or of surrounding tissue.

As used herein, thermal heating mechanisms for neuromodulation include both thermal ablation and non-ablative thermal injury or damage (e.g., via sustained heating or resistive heating). Thermal heating mechanisms may include raising the temperature of target neural fibers above a desired threshold to achieve non-ablative thermal injury, or above a higher temperature) to achieve ablative thermal injury. For example, the target temperature can be above body temperature (e.g., approximately 37° C.) but less than about 45° C. for non-ablative thermal injury, or the target temperature can be about 45° C. for the ablative thermal injury.

As used herein, thermal cooling mechanisms for neuromodulation include non-freezing thermal slowing of nerve conduction and/or non-freezing thermal nerve injury, as well as freezing thermal nerve injury. Thermal cooling mechanisms may include reducing the temperature of target neural fibers below a desired threshold, for example, below the body temperature of about 37° C. (e.g., below about 20° C.) to achieve non-freezing thermal injury. Thermal cooling mechanisms also may include reducing the temperature of the target neural fibers below about 0° C., e.g., to achieve freezing thermal injury.

In addition to monitoring or controlling the temperature during thermal neuromodulation, the length of exposure to thermal stimuli may be specified to affect an extent or degree of efficacy of the thermal neuromodulation. In many embodiments, the length of exposure to thermal stimuli is longer than instantaneous exposure, such as longer than about 30 seconds, or even longer than 2 minutes. In certain specific embodiments, the length of exposure can be less than 10 minutes, but this should in no way be construed as the upper limit of the exposure period. Exposure times measured in hours, days or longer, may be utilized to achieve desired thermal neuromodulation.

When conducting neuromodulation via thermal mechanisms, the temperature threshold discussed previously may be determined as a function of the duration of exposure to thermal stimuli. Additionally or alternatively, the length of exposure may be determined as a function of the desired temperature threshold. These and other parameters may be specified or calculated to achieve and control desired thermal neuromodulation.

In some embodiments, thermally-induced renal neuromodulation may be achieved by directly applying thermal cooling or heating energy to the target neural fibers. For example, a chilled or heated fluid can be applied at least proximate to the target neural fiber, or heated or cooled elements (e.g., a thermoelectric element or a resistive heating element) can be placed in the vicinity of the neural fibers. In other embodiments, thermally-induced renal neuromodulation may be achieved via indirect generation and/or application of the thermal energy to the target neural fibers, such as through application of a 'thermal' electric field, high-intensity focused ultrasound, laser irradiation, etc., to the target neural fibers. For example, thermally-induced renal neuromodulation may be achieved via delivery of a pulsed or continuous thermal electric field to the target neural fibers, the electric field being of sufficient magnitude and/or duration to thermally induce the neuromodulation in the target fibers (e.g., to heat or thermally ablate or necrose the fibers). Additional and alternative methods and apparatus may be utilized to achieve thermally-induced renal neuromodulation, as described hereinafter.

When utilizing thermal heating mechanisms for thermal neuromodulation, protective cooling elements, such as convective cooling elements, optionally may be utilized to protect smooth muscle cells or other non-target tissue from undesired thermal effects during the thermally-induced renal neuromodulation. Likewise, when utilizing thermal cooling mechanisms, protective heating elements, such as convective heating elements, may be utilized to protect the non-target tissue. Non-target tissue additionally or alternatively may be protected by focusing the thermal heating or cooling energy on the target neural fibers so that the intensity of the thermal energy outside of the target zone is insufficient to induce undesired thermal effects in the non-target tissue. When thermal neuromodulation is achieved via thermal energy delivered intravascularly, the non-target tissue may be protected by utilizing blood flow as a conductive and/or convective heat sink that carries away excess thermal energy (hot or cold). For example, when blood flow is not blocked, the circulating blood may remove excess thermal energy from the non-target tissue during the procedure. The intravascularly-delivered thermal energy may heat or cool target neural fibers located proximate to the vessel to modulate the target neural fibers while blood flow within the vessel protects non-target tissue of the vessel wall from the thermal energy. For example, the thermal energy can target neural fibers within the adventitia to necrose or ablate the target fibers, and the blood flow can protect tissue in the vessel wall.

One drawback of using a continuous, intravascularly-delivered thermal energy therapy in the presence of blood flow to achieve desired intravascularly-induced neuromodulation is that the feasible thermal magnitude (e.g., power) and/or duration of the therapy may be limited or insufficient. This can be caused by the limited heat capacity of the blood flowing through the blood vessel to remove excess thermal energy from the vessel wall to mitigate damage or necrosis to the non-target tissue. Pulsed RF electric fields or other type of pulsed thermal energy may facilitate greater thermal magnitude (e.g., higher power), longer total duration and/or better controlled intravascular renal neuromodulation therapy compared to a continuous thermal energy therapy. For example, a pulsed thermal therapy may allow for monitoring of effects of the therapy on target or non-target tissue during the interval between the pulses. This monitoring data optionally may be used in a feedback loop to better control therapy, e.g., to determine whether to continue or stop treatment, and it may facilitate controlled delivery of a higher power or longer duration therapy.

Furthermore, the time interval between delivery of thermal energy pulses may facilitate additional convective or other cooling of the non-target tissue of the vessel wall compared to applying an equivalent magnitude or duration of continuous thermal energy. Without being limited to theory, this may occur because blood flow through the blood vessel may convectively cool (heat) the non-target tissue of the vessel wall with which the blood contacts faster than target neural fibers positioned outside of the vessel.

When providing a pulsed thermal therapy, this difference in the heat transfer rate between the tissue of the blood vessel wall and the relatively remote target neural fibers may be utilized to ablate, necrose or otherwise modulate the target neural fibers without undesirably affecting the non-target tissue. The pulsed thermal energy therapy may be applied with greater thermal magnitude and/or of longer total duration (i.e., the cumulative duration of all thermal energy pulses within the therapy) than a continuous thermal therapy. Heat transfer from the vessel wall to the blood (or vice versa) during the off-time or low-energy interval between the thermal energy pulses facilitates the greater magnitude/longer duration delivery with moderated damage to the non-target tissue.

In addition or as an alternative to utilizing the patient's blood as a heat sink to establish the difference in heat transfer rate, a thermal fluid (hot or cold) may be injected, infused or otherwise delivered into the vessel to remove excess thermal energy and protect the non-target tissues. The thermal fluid may, for example, comprise a saline or other biocompatible fluid that is heated, chilled or at a room temperature. The thermal fluid may, for example, be injected through the device catheter or through a guide catheter at a location upstream from an energy delivery element, or at other locations relative to the tissue for which protection is sought. The thermal fluid may be injected in the presence of blood flow or with the flow temporarily occluded.

Occlusion of flow in combination with thermal fluid delivery may facilitate good control over the heat transfer kinetics along the non-target tissues. For example, the normal variability in blood flow rate between patients, which would vary the heat transfer capacity of the blood flow, may be controlled for by transferring thermal energy between the vessel wall and a thermal fluid that is delivered at a controlled rate. Use of injected thermal fluids to remove excess thermal energy from non-target tissues to relatively protect the non-target tissues during therapeutic treatment of target tissues may be utilized in body lumens other than blood vessels.

In some embodiments, methods and apparatus for real-time monitoring of an extent or degree of neuromodulation or denervation (e.g., an extent or degree of thermal damage) in tissue innervated by the target neural fibers and/or of thermal damage in the non-target tissue may be provided. Likewise, real-time monitoring of the thermal energy delivery element may be provided. Such methods and apparatus may, for example, comprise a thermocouple or other temperature sensor for measuring the temperature of the monitored tissue or of the thermal energy delivery element. Other parameters that can be measured include the power, total energy delivered, or impedance. Monitoring data may be used for feedback control of the thermal therapy. For example, intravascularly-delivered thermal therapy may be monitored and controlled by acquiring temperature or impedance measurements along the wall of the vessel in the vicinity of the treatment zone, and/or by limiting the power or duration of the therapy.

To better understand the structures of several embodiments of devices described below, as well as the methods of using such devices for thermally-induced renal neuromodulation, a description of the renal anatomy in humans is provided.

B. Renal Anatomy Summary

With reference to FIG. 1, the human renal anatomy includes the kidneys K, which are supplied with oxygenated blood by the renal arteries RA. The renal arteries are connected to the heart via the abdominal aorta AA. Deoxygenated blood flows from the kidneys to the heart via the renal veins RV and the inferior vena cava IVC.

Figure 2:
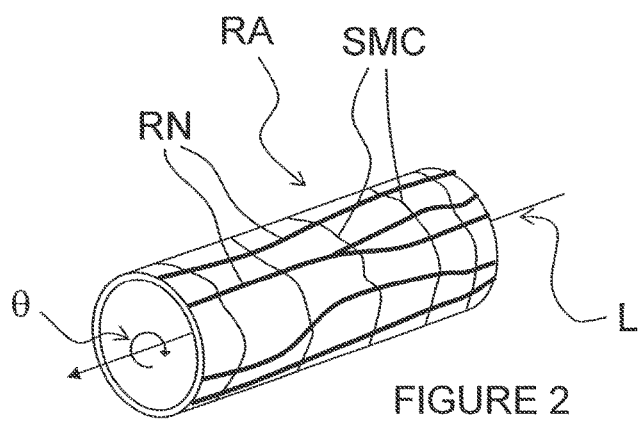
FIG. 2 is a schematic isometric detail view showing the location of the renal nerves relative to the renal artery.

FIG. 2 illustrates a portion of the renal anatomy in greater detail. More specifically, the renal anatomy also includes renal nerves RN extending longitudinally along the lengthwise dimension L of renal artery RA, generally within the adventitia of the artery. The renal artery RA has smooth muscle cells SMC that surround the arterial circumference and spiral around the angular axis of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

C. Embodiments of Apparatus and Methods for Neuromodulation

Figure 3:
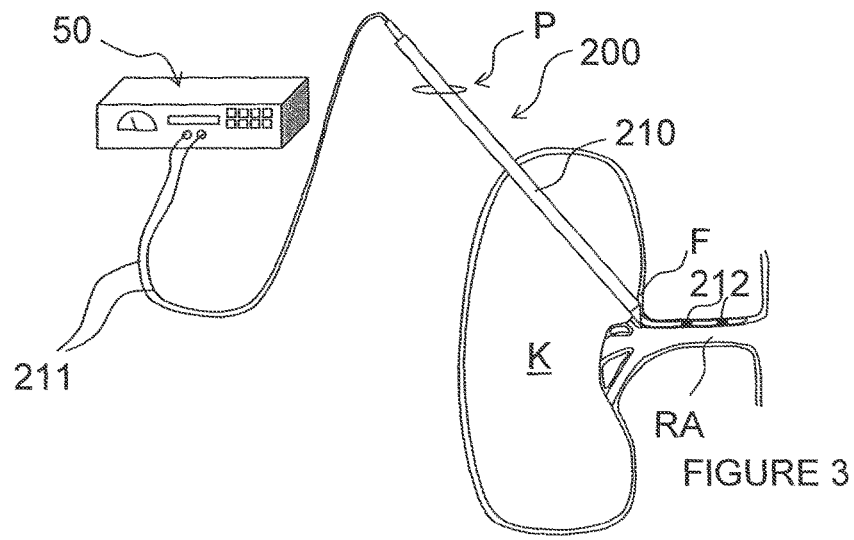
FIG. 3 is a schematic side view, partially in section, illustrating an example of an extravascular method and apparatus for thermal renal neuromodulation.

FIGS. 3-14 illustrate examples of systems and methods for thermally-induced renal neuromodulation. FIG. 3 shows one embodiment of an extravascular apparatus 200 that includes one or more electrodes configured to deliver a thermal electric field to renal neural fibers for renal neuromodulation via heating. The apparatus 200 of FIG. 3 is configured for temporary extravascular placement; however, it should be understood that partially or completely implantable extravascular apparatus additionally or alternatively may be utilized. Applicants have previously described extravascular pulsed electric field systems, for example, in co-pending U.S. patent application Ser. No. 11/189,563, filed Jul. 25, 2005, which has been incorporated herein by reference in its entirety.

The specific embodiment of the apparatus 200 shown in FIG. 3 comprises a laparoscopic or percutaneous system having a probe 210 configured for insertion in proximity to the track of the renal neural supply along the renal artery, vein, hilum and/or within Gerota's fascia under a suitable guidance system. The probe 210 can have at least one electrode 212 for delivering a thermal electric field therapy. The electrode(s) 212, for example, may be mounted on a catheter and electrically coupled to a thermal electric field generator 50 via wires 211. The electrode 212 can be passed through the probe 210, or in an alternative embodiment electrode 212 may be mounted to the probe 210. The probe 210 may have an electrical connector to couple the electrode 212 to the field generator 50.

The field generator 50 is located external to the patient. The generator, as well as any of the electrode embodiments described herein, may be utilized with any embodiment of the present invention for delivery of a thermal electric field with desired field parameters, e.g., parameters sufficient to thermally or otherwise induce renal neuromodulation in target neural fibers via heating and/or electroporation. It should be understood that electrodes of embodiments described hereinafter may be electrically connected to the generator even though the generator is not explicitly shown or described with each embodiment. Furthermore, the field generator optionally may be positioned internally within the patient. Furtherstill, the field generator may additionally comprise or may be substituted with an alternative thermal energy generator, such as a thermoelectric generator for heating or cooling (e.g., a Peltier device), or a thermal fluid injection system for heating or cooling, etc.

The electrode(s) 212 can be individual electrodes that are electrically independent of each other, a segmented electrode with commonly connected contacts, or a continuous electrode. A segmented electrode may, for example, be formed by providing a slotted tube fitted onto the electrode, or by electrically connecting a series of individual electrodes. Individual electrodes or groups of electrodes 212 may be configured to provide a bipolar signal. The electrodes 212 may be dynamically assignable to facilitate monopolar and/or bipolar energy delivery between any of the electrodes and/or between any of the electrodes and a remote electrode. Such a remote electrode may be attached externally to the patient's skin, e.g., to the patient's leg or flank. In FIG. 3, the electrodes 212 comprise a bipolar electrode pair. The probe 210 and the electrodes 212 may be similar to the standard needle or trocar-type used clinically for RF nerve block. Alternatively, the apparatus 200 may comprise a flexible and/or custom-designed probe for the renal application described herein.

In FIG. 3, the probe 210 has been advanced through a percutaneous access site P into proximity with a patient's renal artery RA. The probe pierces the patient's Gerota's fascia F, and the electrodes 212 are advanced into position through the probe and along the annular space between the patient's artery and fascia. Once properly positioned, the target neural fibers may be heated via a pulsed or continuous electric field delivered across the bipolar electrodes 212. Such heating may, for example, ablate or cause non-ablative thermal injury to the target neural fibers to at least partially denervate the kidney innervated by the target neural fibers. The electric field also may induce reversible or irreversible electroporation in the target neural fibers, which may compliment the thermal injury induced in the neural fibers. After treatment, the apparatus 200 may be removed from the patient to conclude the procedure.

Figure 4A:
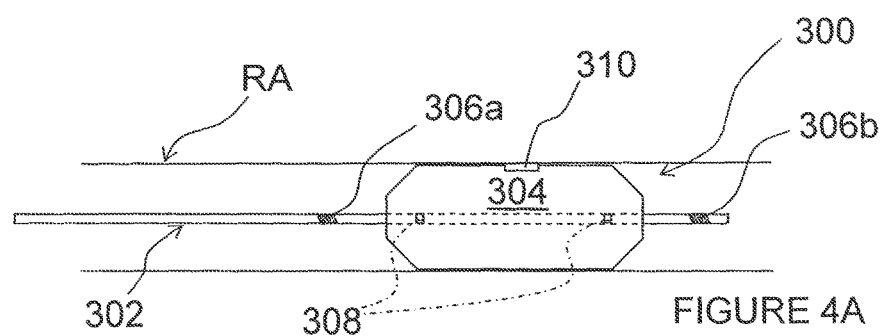
FIGS. 4A-4C are schematic side views, partially in section, illustrating examples of intravascular methods and apparatus for thermal renal neuromodulation.
Figure 4B:
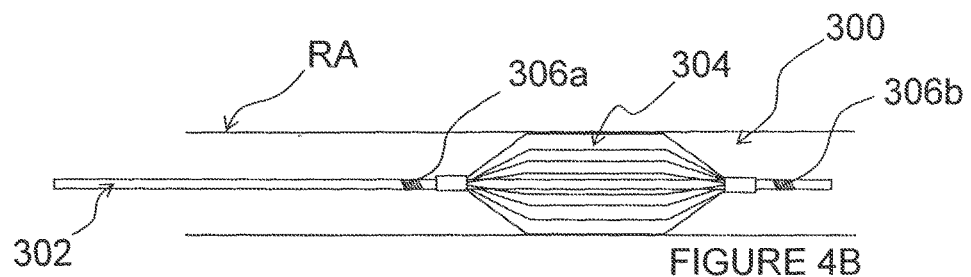

Referring now to FIGS. 4A and 4B, several embodiments of intravascular systems for thermally-induced renal neuromodulation are described. Applicants have previously described intravascular pulsed electric field systems, for example, in co-pending U.S. patent application Ser. No. 11/129,765, filed May. 13, 2005, which has been incorporated herein by reference in its entirety. The embodiments of FIGS. 4A and 4B are apparatus 300 comprising a catheter 302 having an optional positioning element 304, shaft electrodes 306a and 306b disposed along the shaft of the catheter, and optional radiopaque markers 308 disposed along the shaft of the catheter in the region of the positioning element 304. The positioning element 304 can be a balloon, an expandable wire basket, other mechanical expander that holds the electrodes 306a-b at a desired location in the vessel. The electrodes 306a-b can be arranged such that the electrode 306a is near a proximal end of the positioning element 304 and the electrode 306b is near the distal end of the positioning element 304. The electrodes 306 are electrically coupled to the field generator 50 (see FIG. 3) for delivery of a thermal electric field for heating of target neural fibers. In an alternative embodiment, one or more of the electrodes may comprise Peltier electrodes for cooling the target neural fibers to modulate the fibers.

The positioning element 304 optionally may center or otherwise position the electrodes 306a and 306b within a vessel. Additionally, as in FIG. 4A, the positioning element may comprise an impedance-altering element that alters the impedance between electrodes 306a and 306b during the therapy to direct the thermal electric field across the vessel wall. This may reduce an energy required to achieve desired renal neuromodulation and may reduce a risk of undesirably affecting non-target tissue. Applicants have previously described use of a suitable impedance-altering element in co-pending U.S. patent application Ser. No. 11/266,993, filed Nov. 4, 2005, which is incorporated herein by reference in its entirety. When the positioning element 304 comprises an inflatable balloon as in FIG. 4A, the balloon may serve as both a centering element for the electrodes 306 and as an impedance-altering electrical insulator for directing an electric field delivered across the electrodes, e.g., for directing the electric field into or across the vessel wall for modulation of target neural fibers. Electrical insulation provided by the positioning element 304 may reduce the magnitude of applied energy or other parameters of the thermal electric field necessary to achieve desired heating at the target fibers.

Furthermore, the positioning element 304 optionally may be utilized as a cooling element and/or a heating element. For example, the positioning element 304 may be inflated with a chilled fluid that serves as a heat sink for removing heat from tissue that contacts the element. Conversely, the positioning element 304 optionally may be a heating element by inflating it with a warmed fluid that heats tissue in contact with the element. The thermal fluid optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below. The positioning element 304 (or any other portion of apparatus 300) additionally or alternatively may comprise one or more sensors for monitoring the process. In one embodiment, the positioning element 304 has a wall-contact thermocouple 310 (FIG. 4A) for monitoring the temperature or other parameters of the target tissue, the non-target tissue, the electrodes, the positioning element and/or any other portion of the apparatus 300.

Figure 4C:
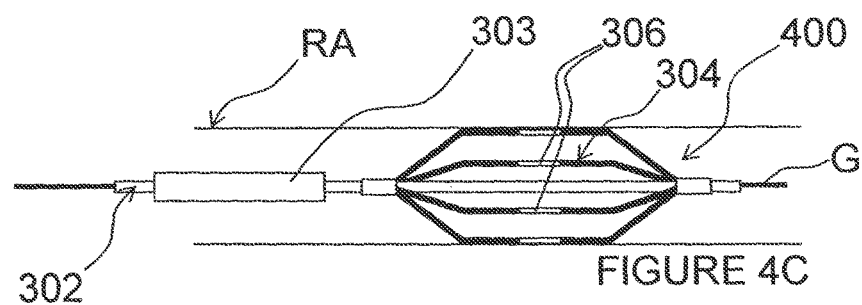

The electrodes 306 can be individual electrodes (i.e., independent contacts), a segmented electrode with commonly connected contacts, or a single continuous electrode. Furthermore, the electrodes 306 may be configured to provide a bipolar signal, or the electrodes 306 may be used together or individually in conjunction with a separate patient ground pad for monopolar use. As an alternative or in addition to placement of the electrodes 306 along the central shaft of the catheter 302, as in FIGS. 4A and 4B, the electrodes 306 may be attached to the positioning element 304 such that they contact the wall of the renal artery RA. In such a variation, the electrodes may, for example, be affixed to the inside surface, outside surface or at least partially embedded within the wall of the positioning element. FIG. 4C, described hereinafter, illustrates one example of wall-contact electrodes, while FIGS. 5-8 illustrate alternative wall-contact electrodes.

In use, the catheter 302 may be delivered to the renal artery RA as shown, or it may be delivered to a renal vein or to any other vessel in proximity to neural tissue contributing to renal function, in a low profile delivery configuration through a guide catheter or other device. Alternatively, catheters may be positioned in multiple vessels for thermal renal neuromodulation, e.g., within both the renal artery and the renal vein. Techniques for pulsed electric field renal neuromodulation in multiple vessels have been described previously, for example, in co-pending U.S. patent application Ser. No. 11/451,728, filed Jul. 12, 2006, which is incorporated herein by reference in its entirety.

Once the positioning element 304 is at a desired location within the renal vasculature, it may be expanded into contact with an interior wall of the vessel. A thermal electric field then may be delivered via the electrodes 306 across the wall of the artery. The electric field thermally modulates the activity along neural fibers that contribute to renal function via heating. In several embodiments, the thermal modulation at least partially denervates the kidney innervated by the neural fibers via heating. This may be achieved, for example, via thermal ablation or non-ablative damage of the target neural fibers. The electric field also may induce electroporation in the neural fibers.

In the embodiment of FIG. 4A, the positioning element 304 illustratively comprises an inflatable balloon, which may preferentially direct the electric field as discussed. In the embodiment of FIG. 4B, the positioning element comprises an expandable wire basket that substantially centers the electrodes 306 within the vessel without blocking blood flow through the vessel. During delivery of the thermal electric field (or of other thermal energy), the blood may act as a heat sink for conductive and/or convective heat transfer to remove excess thermal energy from the non-target tissue. This protects the non-target tissue from undesired thermal effects. This effect may be enhanced when blood flow is not blocked during energy delivery, as in the embodiment of FIG. 4B.

Using the patient's blood as a heat sink is expected to facilitate delivery of longer or greater magnitude thermal treatments with reduced risk of undesired effects to the non-target tissue, which may enhance the efficacy of the treatment at the target neural fibers. Although the embodiment of FIG. 4B illustratively comprises a positioning element for centering the electrodes without blocking flow, it should be understood that the positioning element may be eliminated and/or that the electrodes may be attached to the positioning element such that they are not centered in the vessel upon expansion of the centering element. In such embodiments, the patient's blood may still mitigate excess thermal heating or cooling to protect non-target tissues.

One drawback of using a continuous, intravascularly-delivered thermal energy therapy in the presence of blood flow to achieve desired intravascularly-induced neuromodulation is that the feasible thermal magnitude (e.g., power) and/or duration of the therapy may be limited or insufficient. This can occur because the capacity of the blood to remove heat is limited, and thus the blood flowing through the blood vessel may not remove enough excess thermal energy from the vessel wall to mitigate or avoid undesirable effect in the non-target tissue. Use of a pulsed thermal energy therapy, such as a pulsed thermal RF electric field, may facilitate greater thermal magnitude (e.g., higher power), longer total duration and/or better controlled intravascular renal neuromodulation therapy compared to a continuous thermal energy therapy. For example, the effects of the therapy on target or non-target tissue may be monitored during the intervals between the pulses. This monitoring data optionally may be used in a feedback loop to better control the therapy, e.g., to determine whether to continue or stop treatment, and it may facilitate controlled delivery of a higher power or longer duration therapy.

Furthermore, the off-time or low-energy intervals between thermal energy pulses may facilitate additional convective or other cooling of the non-target tissue of the vessel wall compared to use of a continuous thermal therapy of equivalent magnitude or duration. This may occur because blood flow through the blood vessel can convectively cool (heat) the non-target tissue of the vessel wall faster than the target neural fibers positioned outside of the vessel wall.

When providing a pulsed thermal therapy, the difference in heat transfer rates between tissue of the blood vessel wall and the relatively remote target neural fibers may be utilized to ablate, necrose or otherwise modulate the target neural fibers without producing undesirable effects in the non-target tissue. As a result, the pulsed thermal energy therapy may be applied with greater thermal magnitude and/or of longer total duration (i.e., the cumulative duration of all thermal energy pulses) compared to a continuous thermal therapy. The higher heat transfer rate at the vessel wall during the intervals between the thermal energy pulses facilitates the greater magnitude/longer duration delivery.

In addition or as an alternative to utilizing the patient's blood as a heat sink to create a difference in the heat transfer rate, a thermal fluid (hot or cold) may be injected, infused or otherwise delivered into the vessel to remove excess thermal energy and protect the non-target tissues. The thermal fluid may, for example, comprise saline or another biocompatible fluid that is heated, chilled or at room temperature saline. The thermal fluid may, for example, be injected through the device catheter or through a guide catheter at a location upstream from an energy delivery element, or at other locations relative to the tissue for which protection is sought. The thermal fluid may be injected in the presence of blood flow or with the blood flow temporarily occluded.

In several embodiments, the occlusion of the blood flow in combination with thermal fluid delivery may facilitate good control over the heat transfer kinetics along the non-target tissues. For example, the normal variability in blood flow rate between patients, which would vary the heat transfer capacity of the blood flow, may be controlled for by transferring thermal energy between the vessel wall and a thermal fluid that is delivered at a controlled rate. Furthermore, this method of using an injected thermal fluid to remove excess thermal energy from non-target tissues in order to protect the non-target tissues during therapeutic treatment of target tissues may be utilized in body lumens other than blood vessels.

One or more sensors, such as the thermocouple 310 of FIG. 4A, may be used to monitor the temperature(s) or other parameter(s) at the electrodes 306, the wall of the vessel and/or at other desired locations along the apparatus or the patient's anatomy. The thermal neuromodulation may be controlled using the measured parameter(s) as feedback. This feedback may be used, for example, to maintain the parameter(s) below a desired threshold. For example, the parameter(s) may be maintained below a threshold that may cause undesired effects in the non-target tissues. With blood flowing through the vessel, more thermal energy may be carried away, which may allow for longer or higher energy treatments than when blood flow is blocked in the vessel.

As discussed, when utilizing intravascular apparatus to achieve thermal neuromodulation, in addition or as an alternative to central positioning of the electrode(s) within a blood vessel, the electrode(s) optionally may be configured to contact an internal wall of the blood vessel. Wall-contact electrode(s) may facilitate more efficient transfer of a thermal electric field across the vessel wall to target neural fibers, as compared to centrally-positioned electrode(s). In some embodiments, the wall-contact electrode(s) may be delivered to the vessel treatment site in a reduced profile configuration, then expanded in vivo to a deployed configuration wherein the electrode(s) contact the vessel wall. In some embodiments, expansion of the electrode(s) is at least partially reversible to facilitate retrieval of the electrode(s) from the patient's vessel.

FIG. 4C depicts an embodiment of an apparatus 400 having one or more wall-contact electrodes 306. One or more of the struts of the expandable basket positioning element 304 may comprise a conductive material that is insulated in regions other than along segments that contact the vessel wall and form electrode(s) 306. The electrode(s) may be used in either a bipolar or a monopolar configuration. Furthermore, the electrode(s) may comprise sensor(s), e.g., impedance or temperature sensors, for monitoring and/or controlling the effects of the thermal energy delivery. The sensors, for example, can be thermocouples.

Figure 5A:
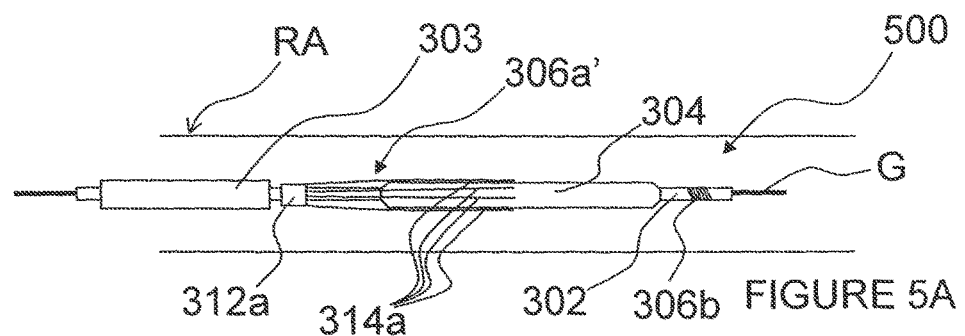
FIGS. 5A and 5B are schematic side views, partially in section, illustrating an alternative embodiment of the intravascular methods and apparatus of FIG. 4 comprising wall-contact electrodes.
Figure 5B:
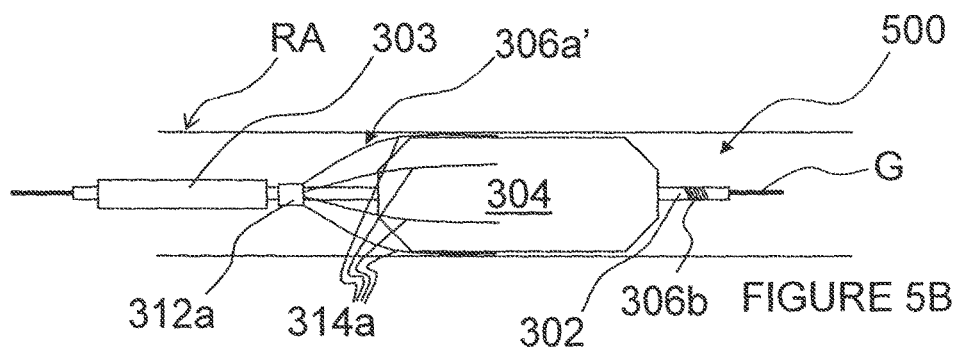

FIGS. 5A and 5B depict an alternative embodiment of intravascular apparatus 500 having electrodes configured to contact the interior wall of a vessel. The apparatus 500 of FIGS. 5A and 5B is an alternative embodiment of the apparatus 300 of FIGS. 4A and 4B wherein the proximal electrode 306a of FIGS. 4A and 4B has been replaced with wall-contact electrode 306a'. The wall-contact electrode comprises proximal connector 312a that connects the electrode to the shaft of the catheter 302 and is electrically coupled to the pulse generator. The apparatus 500 also has a plurality of extensions 314a that extend from the proximal connector 312a and at least partially extend over a surface of positioning element 304. The extensions 314a optionally may be selectively insulated such that only a selective portion of the extensions, e.g., the distal tips of the extensions, are electrically active. The electrode 306a' optionally may be fabricated from a slotted tube, such as a stainless steel or shape-memory (e.g., NiTi) slotted tube. Furthermore, all or a portion of the electrode may be gold-plated to improve radiopacity and/or conductivity.

As seen in FIG. 5A, the catheter 302 may be delivered over a guidewire G to a treatment site within the patient's vessel with the electrode 306a' positioned in a reduced profile configuration. The catheter 302 optionally may be delivered through a guide catheter 303 to facilitate such reduced profile delivery of the wall-contact electrode. When positioned as desired at a treatment site, the electrode 306a' may be expanded into contact with the vessel wall by expanding the positioning element 304 (shown in FIG. 5B). A thermal monopolar or bipolar electric field then may be delivered across the vessel wall and between the electrodes 306a' and 306b to induce thermal neuromodulation, as discussed previously. The optional positioning element 304 may alter impedance within the blood vessel and more efficiently route the electrical energy across the vessel wall to the target neural fibers.

After terminating the electric field, the electrode 306a' may be returned to a reduced profile and the apparatus 300 may be removed from the patient or repositioned in the vessel. For example, the positioning element 304 may be collapsed (e.g., deflated), and the electrode 306a' may be contracted by withdrawing the catheter 302 within the guide catheter 303. Alternatively, the electrode may be fabricated from a shape-memory material biased to the collapsed configuration, such that the electrode self-collapses upon collapse of the positioning element.

Although in FIGS. 5A and 5B the electrode 306a' is expanded into contact with the vessel wall, it should be understood that the electrode alternatively may be fabricated from a self-expanding material biased such that the electrode self-expands into contact with the vessel wall upon positioning of the electrode distal of the guide catheter 303. A self-expanding embodiment of the electrode 306a' may obviate a need for the positioning element 304 and/or may facilitate maintenance of blood flow through the blood vessel during delivery of an electric field via the electrode. After delivery of the electric field, the self-expanding electrode 306a' may be returned to a reduced profile to facilitate removal of the apparatus 300 from the patient by withdrawing the catheter 302 within the guide catheter 303.

Figure 6A:
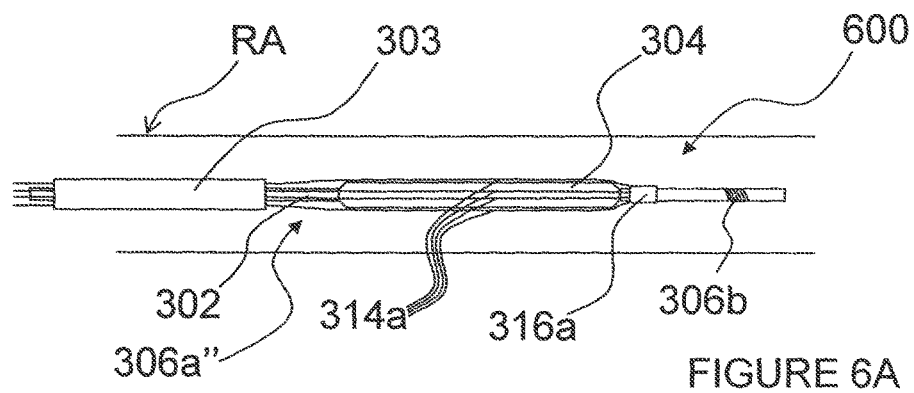
FIGS. 6A and 6B are schematic side views, partially in section, illustrating an additional alternative embodiment of the intravascular methods and apparatus of FIG. 4 comprising alternative wall-contact electrodes.
Figure 6B:
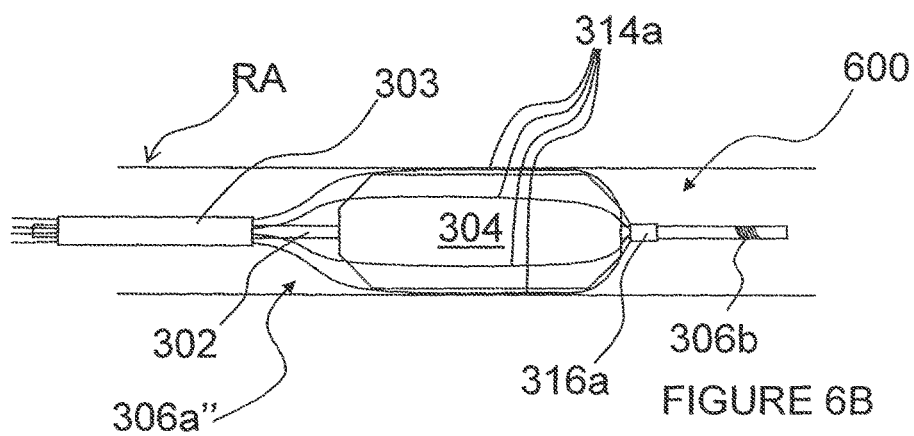

FIGS. 6A and 6B depict another embodiment of an apparatus 600 and methods for delivering a field using a wall-contact electrode. As an alternative to the proximal connector 312a of the electrode 306a' of FIGS. 5A and 5B, the electrode 306a" of FIGS. 6 comprises a distal connector 316a for coupling the electrode to the shaft of catheter 302 on the distal side of the positioning element 304. The distal connector enables the electrode to extend over the entirety of the positioning element 304 and may facilitate contraction of the electrode 306a" after thermal neuromodulation. For example, the electrode 306a" can be contracted by proximally retracting the proximal connector 312a relative to the catheter 302 during or after contraction of the positioning element 304. FIG. 6A shows the electrode 306a" in the reduced profile configuration, and FIG. 6B shows the electrode in the expanded in which the conductive portions contact the vessel wall.

Figure 7A:
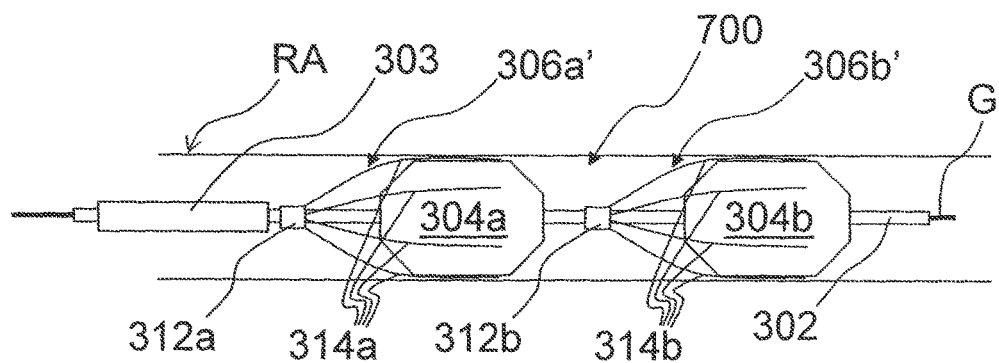
FIGS. 7A and 7B are schematic side views, partially in section, illustrating other alternative embodiments of the intravascular methods and apparatus of FIG. 4 comprising multiple wall-contact electrodes.
Figure 7B:
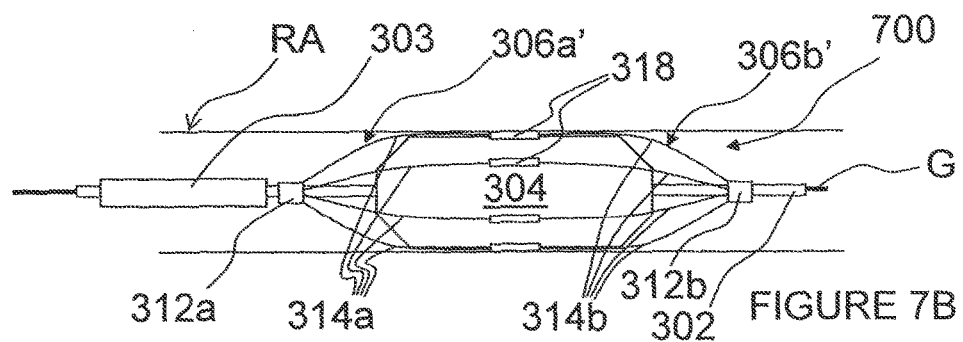

FIGS. 7A and 7B show additional alternative embodiments of methods and an apparatus 700. In FIGS. 7A and 7B, the apparatus 700 comprises the proximal electrode 306a' of FIGS. 5A and 5B, and a distal wall-contact electrode 306b'. The embodiment of FIG. 7A comprises proximal and distal positioning elements 304a and 304b, respectively, for expanding the proximal and distal wall-contact electrodes 306a' and 306b', respectively, into contact with the vessel wall. The embodiment of FIG. 7B comprises only a single positioning element 304, but the distal wall-contact electrode 306b' is proximal facing and positioned over the distal portion of the positioning element 304 to facilitate expansion of the distal electrode 306b'. In the embodiment of FIG. 7B, the extensions of the proximal and distal electrodes optionally may be connected along non-conductive connectors 318 to facilitate collapse and retrieval of the electrodes post-treatment.

A bipolar electric field may be delivered between the proximal and distal wall-contact electrodes, or a monopolar electric field may be delivered between the proximal and/or distal electrode(s) and an external ground. Having both the proximal and distal electrodes in contact with the wall of the vessel may facilitate more efficient energy transfer across the wall during delivery of a thermal electric field, as compared to having one or both of the proximal and distal electrodes centered within the vessel.

FIGS. 8A-8H illustrate additional embodiments of the apparatus and methods that can comprise one or more wall-contact electrodes, blood flow occlusion features, and thermal fluid injection functions. The embodiments of FIG. 8 are described as monopolar devices, but it should be understood that any or all of the embodiments may be configured or operated as bipolar devices. Furthermore, although blood flow occlusion and thermal fluid injection are described in combination with wall-contact electrode(s), it should be understood that such occlusion and injection features may be provided in combination with electrode(s) that do not contact the vessel wall.

As discussed previously, in addition or as an alternative to utilizing the patient's blood as a heat sink to create different heat transfer rates between target neural fibers and non-target tissue of the wall of the vessel within which thermal energy is delivered, a thermal fluid (hot or cold) may be injected, infused or otherwise delivered into the vessel. The thermal fluid may further remove excess thermal energy and protect the non-target tissues. When delivering thermal RF therapy, for example, the thermal fluid may, for example, comprise chilled or room temperature saline (e.g., saline at a temperature lower than the temperature of the vessel wall during the therapy delivery). The thermal fluid may be injected through the device catheter or through a guide catheter at a location upstream from an energy delivery element, or at other locations relative to the tissue for which protection is sought. The thermal fluid may be injected in the presence of blood flow or with blood flow temporarily occluded. The occlusion of blood flow in combination with thermal fluid delivery may facilitate good control over the heat transfer kinetics along the non-target tissues, as well as injection of fluid from a downstream location.

Figure 8A:
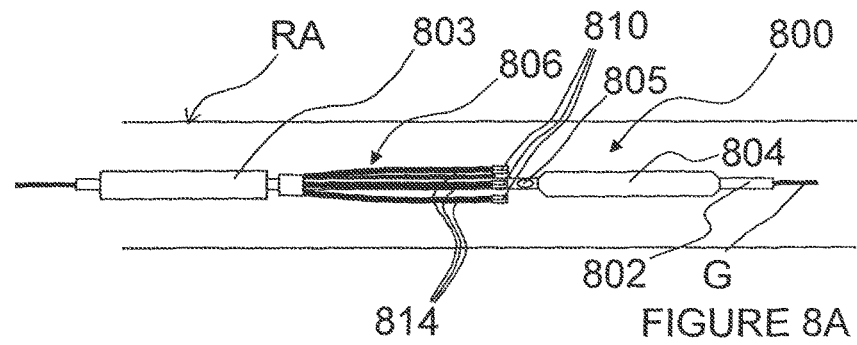
FIGS. 8A-8H are schematic side views, partially in section, illustrating embodiments of the intravascular methods and apparatus of FIG. 4 comprising one or more wall-contact electrodes, as well as optional blood flow occlusion and thermal fluid injection.
Figure 8B:
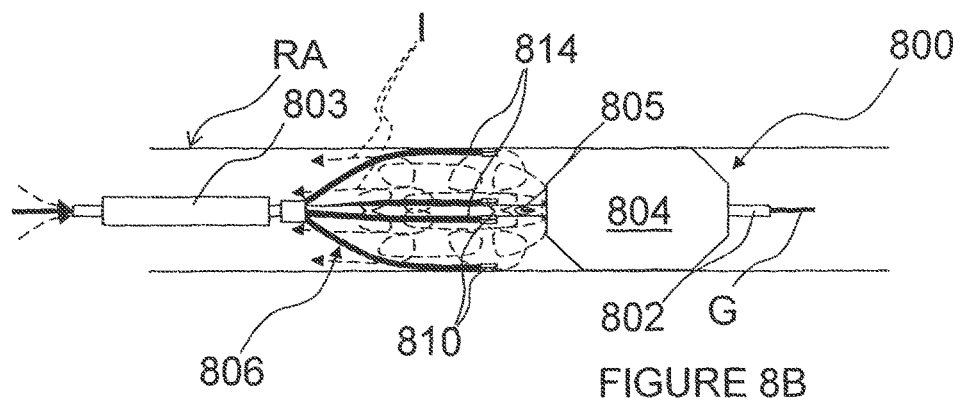

FIGS. 8A and 8B show an embodiment of an apparatus 800a that comprises the catheter 802 having an element 804, which may be used to position the apparatus within the vessel and/or to occlude blood flow. The element 304 can be an inflatable balloon. The apparatus 800 can further have an active monopolar electrode 806 located proximally from the element 304 such that inflation of the element 304 blocks blood flow downstream of the electrode 806. The monopolar electrode 806 illustratively comprises multiple extensions 814, and it should be understood that any desired number of extensions may be provided, including a single extension. The monopolar electrode is utilized in combination with a remote electrode, such as a ground pad, positioned external to the patient. The apparatus can also comprise an infusion port 805 between the element 804 and the monopolar electrode 806.

In FIG. 8A, the catheter 802 may be advanced within the renal artery RA in a reduced profile delivery configuration. In FIG. 8B, once properly positioned, the electrode 806 may be actively expanded, or it may self-expand by removing a sheath, the guide catheter or another type of restraint from the electrode. The expanded electrode 806 contacts the vessel wall. The element 804 may be expanded (before, during or after expansion of the electrode) to properly position the electrode within the vessel and/or to occlude blood flow within the renal artery downstream of the electrode. A monopolar electric field may be delivered between the active electrode 806 and the external ground. The electric field may, for example, comprise a pulsed or continuous RF electric field that thermally induces neuromodulation (e.g., necrosis or ablation) in the target neural fibers.

The thermal therapy may be monitored and controlled, for example, via data collected with thermocouples 810, impedance sensors or other sensors.

To increase the power that may be delivered or the duration of the thermal treatment without undesirably affecting non-target tissue, a thermal fluid infusate I may be injected through injection port 805 of the catheter 802 to cool (heat) the non-target tissue. This is expected to mitigate undesired effects in the non-target tissue. The infusate may, for example, comprise chilled saline that removes excess thermal energy (hot or cold) from the wall of the vessel during thermal RF therapy.

Convective or other heat transfer between the non-target vessel wall tissue and the infusate I may facilitate cooling (heating) of the vessel wall at a faster rate than cooling (heating) occurs at the target neural fibers. This difference in the heat transfer rates between the wall of the vessel and the target neural fibers may be utilized to modulate the neural fibers. Furthermore, when utilizing a pulsed thermal therapy, the accelerated heat transfer at the wall relative to the neural fibers may allow for relatively higher power or longer duration therapies (as compared to continuous thermal therapies). Also, the interval between pulses may be used to monitor and/or control effects of the therapy.

Figure 8C:
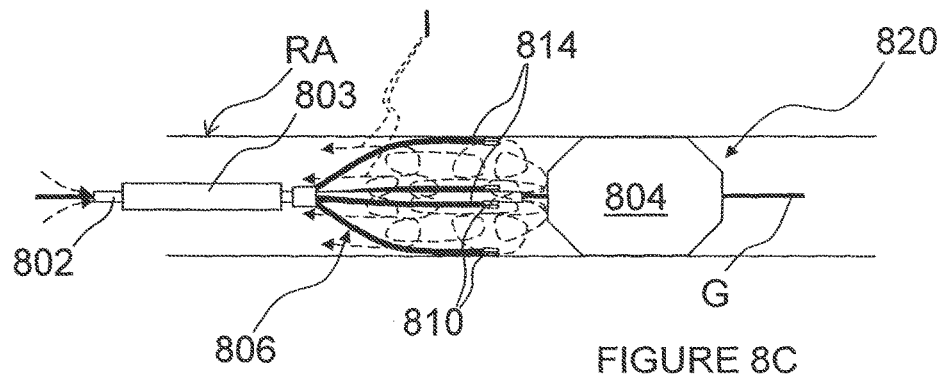
Figure 8D:
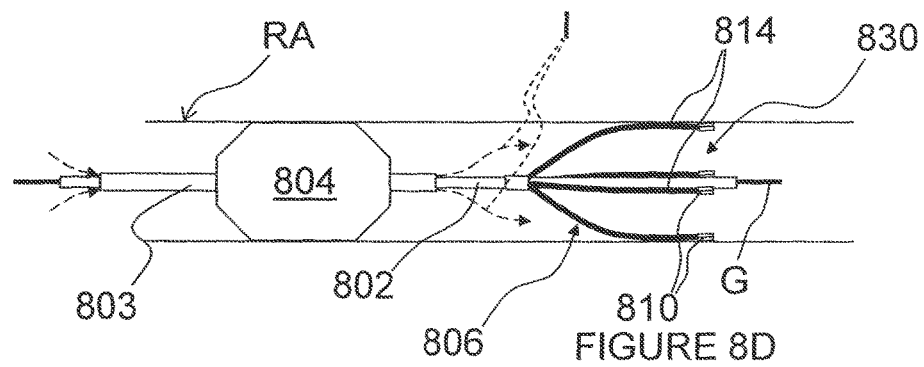

FIG. 8C shows an embodiment of another apparatus 801 with wall-contact electrodes, flow occlusion and thermal fluid injection. In FIG. 8C, the occlusion element 804 is coupled to the guide wire G, which may comprise an inflation lumen, and the infusate I is delivered through a distal outlet of the catheter 802. As will be apparent, the occlusion element alternatively may be coupled to a separate catheter or sheath rather than to the guide wire. Also, the infusate may, for example, be delivered through the guide wire lumen or through an additional lumen or annulus of the catheter 802. FIG. 8D illustrates another embodiment of an apparatus 830 wherein the occlusion element 804 is positioned proximal or upstream of the electrode(s) 806, and the infusate I is delivered at a position distal of the occlusion element but proximal of the electrode(s).

Figure 8E:
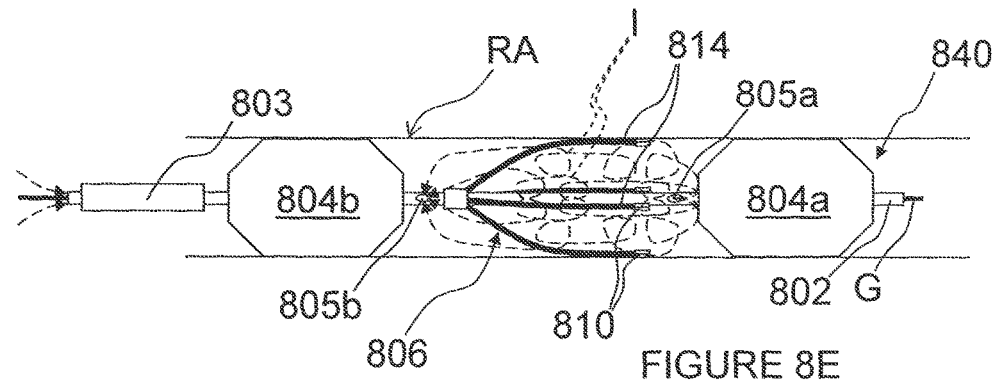

FIG. 8E is an embodiment of apparatus 804 with occlusion elements 804 positioned both proximal and distal of the electrode(s) 306. In addition to having a first injection port 305*a*, the catheter 302 comprises an aspiration port 305*b*. Separate lumens can extend through the catheter for injection and aspiration of the infusate I via the ports 305. Providing both injection and aspiration of the infusate facilitates good control over the flow dynamics of the infusate, and thereby the heat transfer kinetics of the infusate. For example, providing aspiration and injection at the same rate may provide consistent heat transfer kinetics between the vessel and the electrode(s).

Figure 8F:
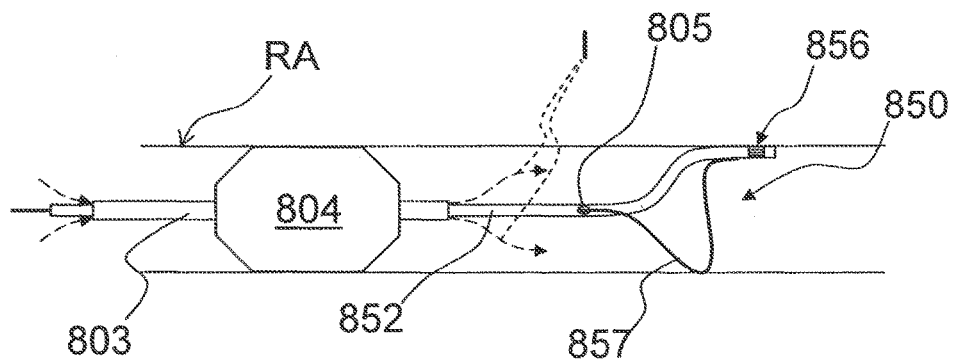

FIG. 8F illustrates another embodiment of an apparatus 850 having a catheter 852 comprising a wall-contact electrode 856 that may be moved into contact with the vessel wall via an elongated member 857. In this embodiment, the elongated member 857 is distally connected to the catheter in the vicinity of the electrode 306. The elongated member may be configured for self expansion, or it may extend through port 305 of the catheter 302 and through a lumen of the catheter to a proximal location for manipulation by a medical practitioner. The proximal section of the elongated member may be advanced relative to the catheter 302 by the medical practitioner such that the member assumes the illustrated curved profile.

Upon expansion of the elongated member, the catheter 302 is deflected such that the electrode 306 coupled to the catheter shaft contacts the vessel wall. Optionally, element 304 may be expanded to facilitate positioning of the electrode via the elongated member and/or to block flow through the vessel. The element 304 can be coupled to the guide or delivery catheter 303. Infusate I optionally may be delivered through the catheter 303 as shown.

Figure 8G:
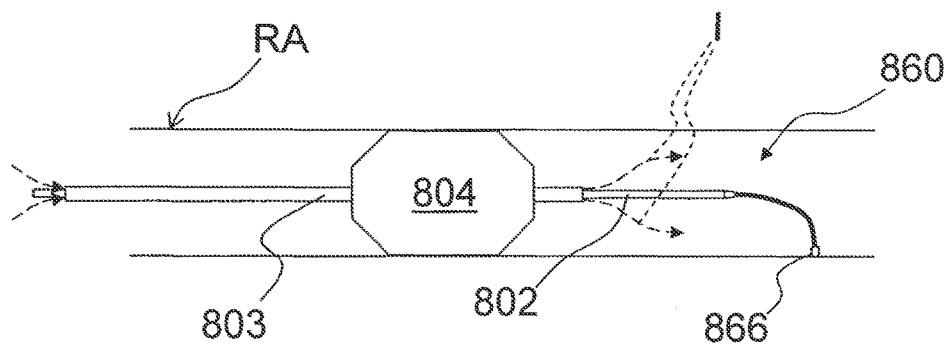
Figure 8H:
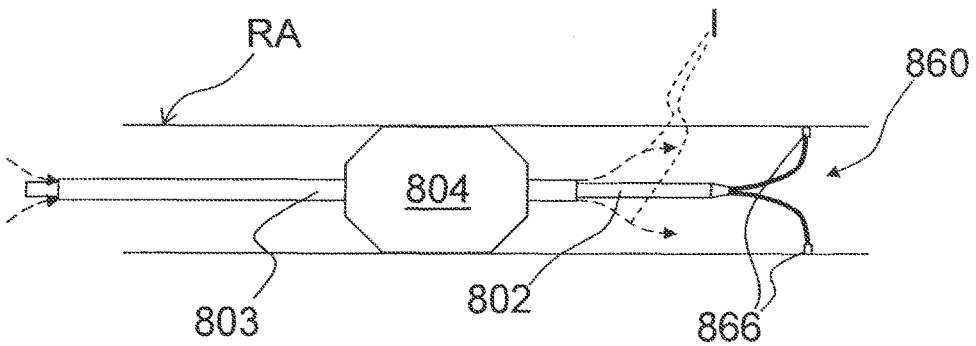

FIG. 8G is an embodiment of an apparatus 860 comprising a shaped or self-expanding electrode 866. The electrode 866 may be delivered to a treatment site within catheter 303, and then it moves to a preselected shape after it has been removed from the lumen of the catheter 303. For example, the electrode 866 can be removed from the catheter by advancing the catheter 302 and/or retracting the catheter 303. The electrode 866 contacts the vessel wall for delivery of therapy. Optionally, catheter 302 may be rotated to rotate the electrode relative to the vessel wall and angularly reposition the electrode. The therapy may be delivered at a singular angular position or at multiple angular positions. Additionally or alternatively, multiple angularly spaced electrodes 306 may be positioned within the vasculature, as shown in FIG. 8H. In addition to angular spacing, the electrodes may be longitudinally spaced to facilitate treatment over a longitudinal segment of the vessel, e.g., to achieve a circumferential treatment along the longitudinal segment rather than along a cross-section.

In addition to extravascular and intravascular systems for thermally-induced renal neuromodulation, intra-to-extravascular systems may be provided. The intra-to-extravascular systems may, for example, have electrode(s) that are delivered to an intravascular position, and then at least partially passed through/across the vessel wall to an extravascular position prior to delivery of a thermal electric field. Intra-to-extravascular positioning of the electrode(s) may place the electrode(s) in closer proximity to target neural fibers for delivery of a thermal electric field, as compared to fully intravascular positioning of the electrode(s). Applicants have previously described intra-to-extravascular pulsed electric field systems, for example, in co-pending U.S. patent application Ser. No. 11/324,188, filed Dec. 29, 2005, which is incorporated herein by reference in its entirety.

Figure 9:
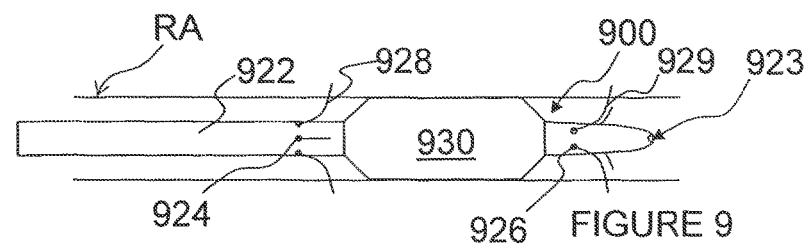
FIG. 9 is a schematic side view, partially in section, illustrating an example of an intra-to-extravascular method and apparatus for thermal renal neuromodulation.

FIG. 9 illustrates one embodiment of an intra-to-extravascular ("ITEV") system for thermally-induced renal neuromodulation is described. ITEV system 900 comprising a catheter 922 having (a) a plurality of proximal electrode lumens terminating at proximal side ports 924, (b) a plurality of distal electrode lumens terminating at distal side ports 926, and (c) a guidewire lumen 923. The catheter 922 preferably comprises an equal number of proximal and distal electrode lumens and side ports. The ITEV system 900 also includes proximal needle electrodes 928 that may be advanced through the proximal electrode lumens and the proximal side ports 924, as well as distal needle electrodes 929 that may be advanced through the distal electrode lumens and the distal side ports 926.

The catheter 922 comprises an optional expandable positioning element 930, which may comprise an inflatable balloon or an expandable basket or cage. In use, the positioning element 930 may be expanded prior to deployment of the needle electrodes 928 and 929 in order to position or center the catheter 922 within the patient's vessel (e.g., within renal artery RA). Centering the catheter 922 is expected to facilitate delivery of all needle electrodes to desired depths within/external to the patient's vessel (e.g., to deliver all of the needle electrodes approximately to the same depth). In FIG. 9, the illustrated positioning element 930 is between the proximal side ports 924 and the distal side ports 926, and thus the positioning element 930 is between the delivery positions of the proximal and distal electrodes. However, it should be understood that the positioning element 930 additionally or alternatively may be positioned at a different location or at multiple locations along the length of the catheter 922 (e.g., at a location proximal of the side ports 924 and/or at a location distal of the side ports 926).

As illustrated in FIG. 9, the catheter 922 may be advanced to a treatment site within the patient's vasculature over a guidewire (not shown) via the lumen 323. During intravascular delivery, the electrodes 928 and 929 may be positioned such that their non-insulated and sharpened distal regions are positioned within the proximal and distal lumens, respectively. Once at a treatment site, a medical practitioner may advance the electrodes via their proximal regions that are located external to the patient. Such advancement causes the distal regions of the electrodes 928 and 929 to exit side ports 924 and 926, respectively, and pierce the wall of the patient's vasculature such that the electrodes are positioned extravascularly via an ITEV approach.

The proximal electrodes 928 can be connected to an electric field generator 50 as active electrodes, and the distal electrodes 929 can serve as return electrodes. In this manner, the proximal and distal electrodes form bipolar electrode pairs that align the thermal electric field with a longitudinal axis or direction of the patient's vasculature. As will be apparent, the distal electrodes 929 alternatively may comprise the active electrodes and the proximal electrodes 928 may comprise the return electrodes. Furthermore, the proximal and/or the distal electrodes may comprise both active and return electrodes. Furtherstill, the proximal and/or the distal electrodes may be utilized in combination with an external ground for delivery of a monopolar thermal electric field. Any combination of active and distal electrodes may be utilized, as desired.

When the electrodes 928 and 929 are connected to an electric field generator and positioned extravascularly, and with the positioning element 930 optionally expanded, delivery of the thermal electric field may proceed to achieve desired renal neuromodulation via heating. The electric field also may induce electroporation. After achievement of the thermally-induced renal neuromodulation, the electrodes may be retracted within the proximal and distal lumens, and the positioning element 930 may be collapsed for retrieval. The ITEV system 920 then may be removed from the patient to complete the procedure. Additionally or alternatively, the system may be repositioned to provide therapy at another treatment site, such as to provide bilateral renal neuromodulation.

Cooling elements, such as convective cooling elements, may be utilized to protect non-target tissues like smooth muscle cells from thermal damage during thermally-induced renal neuromodulation via heat generation. Non-target tissues may be protected by focusing the thermal energy on the target neural fibers such that an intensity of the thermal energy is insufficient to induce thermal damage in non-target tissues distant from the target neural fibers.

Although FIGS. 3-7 and 9 illustratively show bipolar apparatus, it should be understood that monopolar apparatus alternatively may be utilized as in FIGS. 8A-8H. For example, an active monopolar electrode may be positioned intravascularly, extravascularly or intra-to-extravascularly in proximity to target neural fibers that contribute to renal function. A return electrode may be attached to the exterior of the patient or positioned in the patient apart from the active electrodes. Finally, a thermal electric field may be delivered between the in vivo monopolar electrode and the remote electrode to effectuate desired thermally-induced renal neuromodulation. Monopolar apparatus additionally may be utilized for bilateral renal neuromodulation.

The embodiments of FIGS. 3-9 illustratively describe methods and apparatus for thermally-induced renal neuromodulation via delivery of thermal electric fields that modulate the target neural fibers. However, it should be understood that alternative methods and apparatus for thermally-induced (via both heating and cooling) renal neuromodulation may be provided. For example, electric fields may be used to cool and modulate the neural fibers with thermoelectric or Peltier elements. Also, thermally-induced renal neuromodulation optionally may be achieved via direct application of thermal energy to the target neural fibers. Such direct thermal energy may be generated and/or transferred in a variety of ways, such as via resistive heating, via delivery of a heated or chilled fluid (see FIGS. 10 and 12), via a Peltier element (see FIG. 11), etc. Thermally-induced renal neuromodulation additionally or alternatively may be achieved via application of high-intensity focused ultrasound to the target neural fibers (see FIG. 13). Additional and alternative methods and apparatus for thermally-induced renal neuromodulation may be used in accordance with the present invention.

Figure 10:
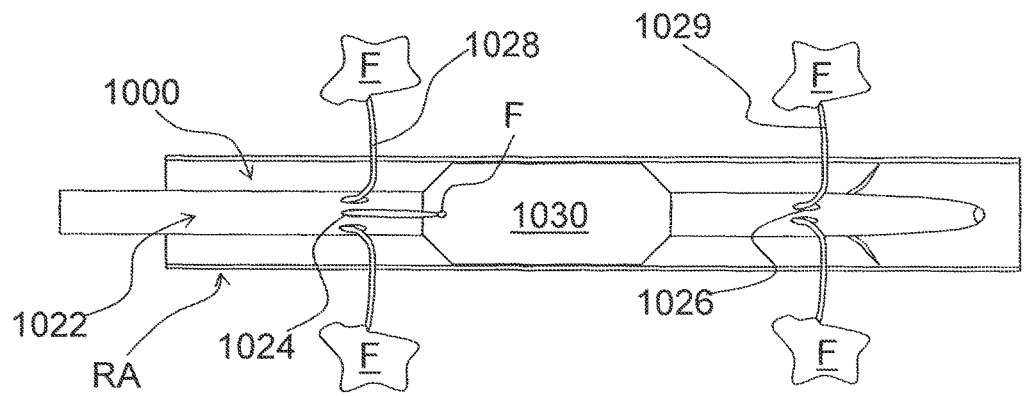
FIG. 10 is a schematic side view, partially in section, of an alternative embodiment of the method and apparatus of FIG. 8 configured for thermal renal neuromodulation via direct application of thermal energy.

With reference now to FIG. 10, an alternative embodiment of an apparatus 1000 and methods for thermally-induced neuromodulation via direct application of thermal energy is described. In the embodiment of FIG. 10, the electrodes 328 and 329 of FIG. 9 have been replaced with infusion needles 1028 and 1029, respectively. A thermal fluid F may be delivered through the needles to the target neural fibers. The thermal fluid may be heated in order to raise the temperature of the target neural fibers above a desired threshold. For example, the temperature of the neural fibers can be raised above a body temperature of about 37° C., or above a temperature of about 45° C. Alternatively, the thermal fluid may be chilled to reduce the temperature of the target neural fibers below a desired threshold. For example, the neural fibers can be cooled to below the body temperature of about 37° C., or further cooled below about 20° C., or still further cooled below a freezing temperature of about 0° C. As will be apparent, in addition to intra-to-extravascular delivery of a thermal fluid, the thermal fluid may be delivered intravascularly (e.g., may inflate and/or be circulated through a balloon member), extravascularly (e.g., may be circulated through a vascular cuff), or a combination thereof.

In addition or as alternative to injection of a thermal fluid to the target neural fibers through infusion needles 1028 and 1029, an alternative neuromodulatory agent, such as a drug or medicament, may be injected to modulate, necrose or otherwise block or reduce transmission along the target neural fibers. Examples of alternative neuromodulatory agents include, but are not limited to, phenol and neurotoxins, such as botulinum toxin. Additional neuromodulatory agents, per se known, will be apparent to those of skill in the art.

Figure 11:
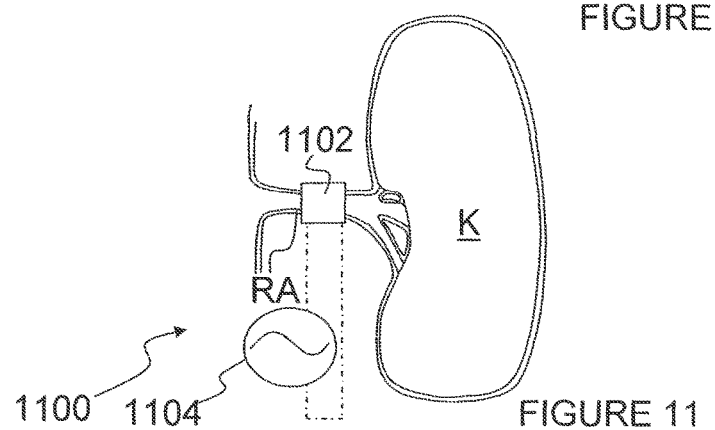
FIG. 11 is a schematic side view, partially in section, illustrating a method and apparatus for thermal renal neuromodulation comprising a thermoelectric element suitable for direct application of thermal energy to target neural fibers.

FIG. 11 shows another method and apparatus 110 for thermal renal neuromodulation via direct application of thermal energy to the target neural fibers. The apparatus 1100 comprises renal artery cuff 1102 having one or more integrated thermoelectric elements that are electrically coupled to an internal or external power supply 1104. The thermoelectric element utilizes the well-known Peltier effect (i.e., the establishment of a thermal gradient induced by an electric voltage) to achieve thermal renal neuromodulation.

An electric current is passed from the power supply 1104 to the thermoelectric element of the cuff 1102. The thermoelectric element can comprise two different metals (e.g., a p-type and an n-type semiconductor) that are connected to each other at two junctions. The current induces a thermal gradient between the two junctions, such that one junction cools while the other is heated. Reversal of the polarity of the voltage applied across the two junctions reverses the direction of the thermal gradient. Either the hot side or the cold side of the thermoelectric element faces radially inward in order to heat or cool, respectively, the target neural fibers that travel along the renal artery to achieve thermal renal neuromodulation. Optionally, the radially outward surface of the thermoelectric element may be insulated to reduce a risk of thermal damage to the non-target tissues. The cuff 1102 may comprise one or more temperature sensors, such as thermocouples, for monitoring the temperature of the target neural fibers and/or of the non-target tissues.

Figure 12:
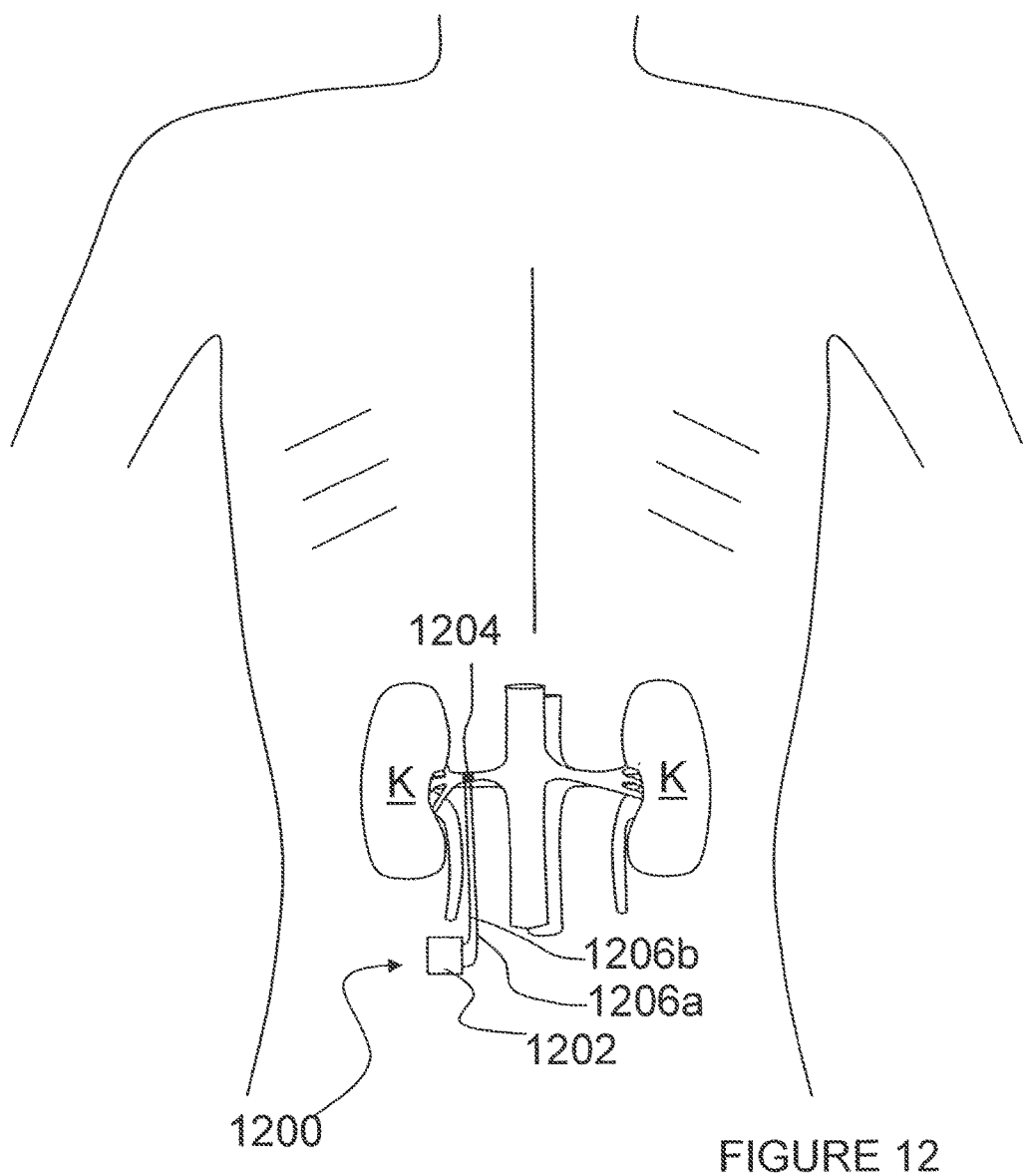
FIG. 12 is a schematic side view, partially in section, illustrating another method and apparatus for thermal renal neuromodulation comprising a thermoelectric element.

FIG. 12 shows another method and apparatus 1200 utilizing the Peltier effect. The apparatus 1200 comprises an implanted or external pump 1202 connected to a renal artery cuff 1204 via inlet fluid conduit 1206*a* and outlet fluid conduit 1206*b*. The inlet fluid conduit transfers fluid from the pump to the cuff, while the outlet fluid conduit transfers fluid from the cuff to the pump to circulate fluid through the cuff. A reservoir of fluid may be located in the cuff, the pump and/or in the fluid conduits.

The pump 1202 further comprises one or more thermoelectric or other thermal elements in heat exchange contact with the fluid reservoir for cooling or heating the fluid that is transferred to the cuff to thermally modulate the target neural fibers. The apparatus 1200 optionally may have controls for automatic or manual control of fluid heating or cooling, as well as fluid circulation within the cuff. Furthermore, the apparatus may comprise temperature and/or renal sympathetic neural activity monitoring or feedback control. Although the apparatus illustratively is shown unilaterally treating neural fibers innervating a single kidney, it should be understood that bilateral treatment of neural fibers innervating both kidneys alternatively may be provided.

Figure 13A:
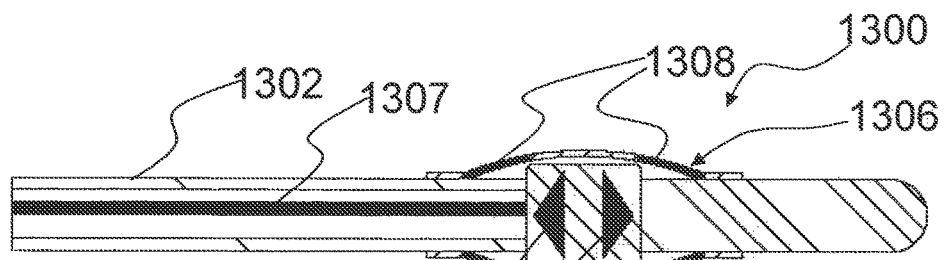
FIGS. 13A and 13B are schematic side views, partially in section, illustrating a method and apparatus for thermal renal neuromodulation via high-intensity focused ultrasound.

Thermal renal neuromodulation alternatively may be achieved via pulsed or continuous high-intensity focused ultrasound. High intensity focused ultrasound also may induce reversible or irreversible electroporation in the target neural fibers. Furthermore, the ultrasound may be delivered over a full 360° (e.g. when delivered intravascularly) or over a radial segment of less than 360° (e.g., when delivered intravascularly, extravascularly, intra-to-extravascularly, or a combination thereof). FIGS. 13A and B illustrate an embodiment of an ultrasonic apparatus 1300 comprising a catheter 1302, one or more ultrasound transducers 1304 positioned along the shaft of the catheter, and an inflatable balloon 1306 around the transducers 1304. The ultrasound transducers 1304 are coupled to an ultrasound signal generator via conductors 1307. The balloon 1306 can have an acoustically reflective portion 1308 for reflecting an ultrasound wave and an acoustically transmissive portion 1309 the wave through which the ultrasonic energy can pass. In this manner, the wave may be focused as shown at a focal point or radius P positioned a desired focal distance from the catheter shaft. In an alternative embodiment, the transducers may be attached directly to the balloon.

The focal distance may be specified or dynamically variable such that the ultrasonic wave is focused at a desired depth on target neural fibers outside of the vessel. For example, a family of catheter sizes may be provided to allow for a range of specified focal distances. A dynamically variable focal distance may be achieved, for example, via calibrated expansion of the balloon.

Figure 13B:
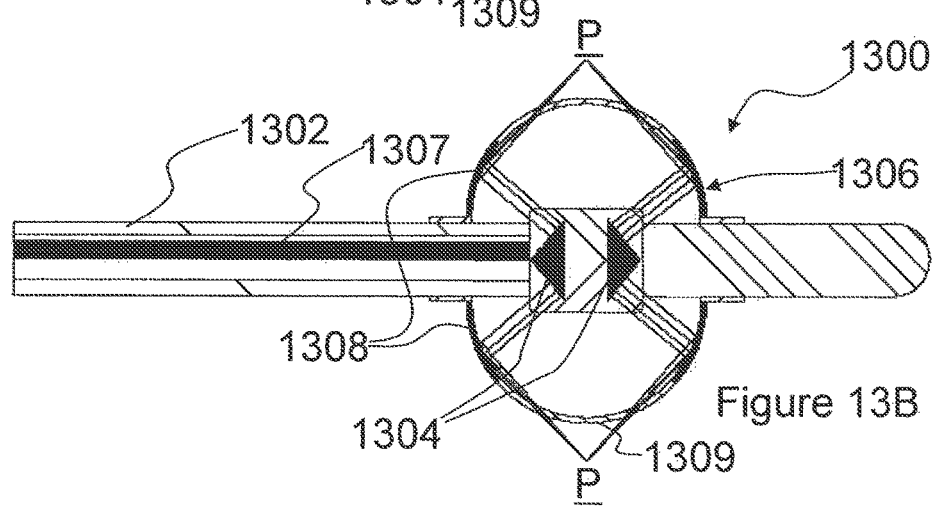

Focusing the ultrasound wave may produce a reverse thermal gradient that protects the non-target tissues and selectively affect the target neural fibers to achieve thermal renal neuromodulation via heating. As a result, the temperature at the vessel wall may be less than the temperature at the target tissue. FIG. 13A shows the apparatus 1300 in a reduced delivery and retrieval configuration, and FIG. 13B shows the apparatus 1300 in an expanded deployed configuration.

Figure 14:
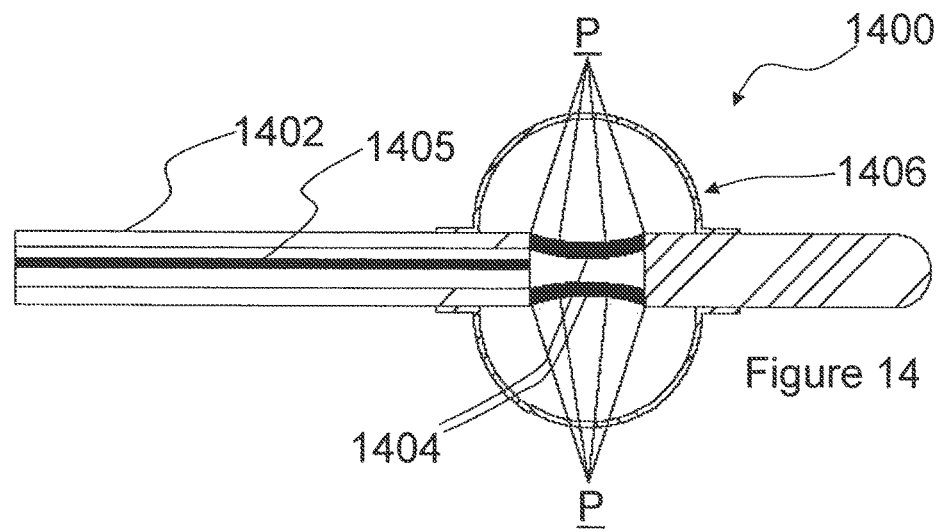
FIG. 14 is a schematic side view, partially in section, illustrating an alternative embodiment of the apparatus and method of FIG. 13.

FIG. 14 shows an alternative embodiment of an ultrasonic 1400 having a catheter 1402, a conductor 1403, and concave ultrasound transducers 1401. The concave ultrasound transducers 1404 direct the energy to a specific focal point P. A such, the concave transducers 1404 are self-focusing and eliminate need of the reflective portion of the balloon 366 (e.g., the balloon may be acoustically transmissive at all points).

The apparatus described above with respect to FIGS. 3-14 optionally may be used to quantify the efficacy, extent or cell selectivity of thermally-induced renal neuromodulation in order to monitor and/or control the neuromodulation. As discussed previously, the apparatus may further comprise one or more sensors, such as thermocouples or imaging transducers, for measuring and monitoring one or more parameters of (a) the apparatus, (b) target neural fibers and/or (c) non-target tissues. For example, a temperature rise or drop above or below certain thresholds is expected to thermally ablate, non-ablatively injure, freeze or otherwise damage the target neural fibers to thereby modulate the target neural fibers.

Figure 15A:
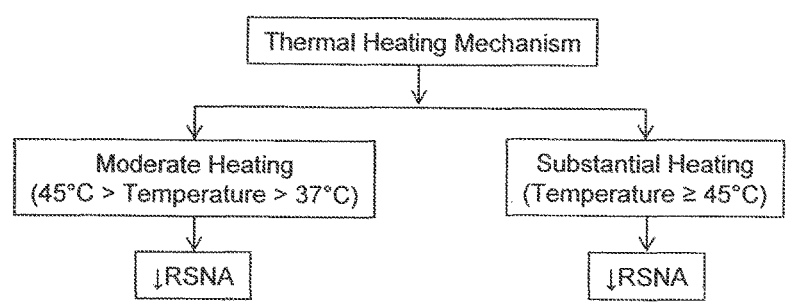
FIGS. 15A and 15B are schematic diagrams for classifying the various types of thermal neuromodulation that may be achieved with the apparatus and methods of the present invention.
Figure 15B:
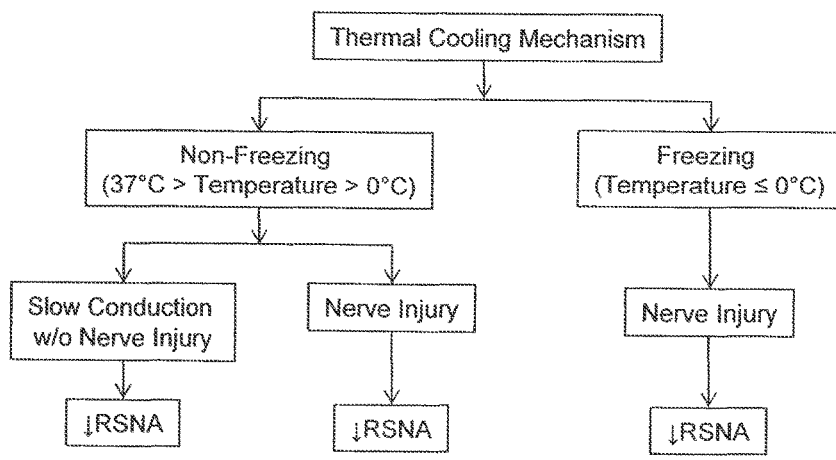

FIGS. 15A and 15B classify the various types of thermal neuromodulation that may be achieved with the apparatus and methods of the present invention. FIGS. 15A and 15B are provided only for the sake of illustration and should in no way be construed as limiting. FIG. 15A classifies thermal neuromodulation due to heat exposure. As shown, exposure to heat in excess of a body temperature of about 37° C., but below a temperature of about 45° C., may induce thermal injury via moderate heating of the target neural fibers or of vascular structures that perfuse the target fibers. For example, this may induce non-ablative thermal injury in the fibers or structures. Exposure to heat above a temperature of about 45° C., or above about 60° C., may induce thermal injury via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

As seen in FIG. 15B, thermal cooling for neuromodulation includes non-freezing thermal slowing of nerve conduction and/or nerve injury, as well as freezing thermal nerve injury. Non-freezing thermal cooling may include reducing the temperature of the target neural fibers or of the vascular structures that feed the fibers to temperatures below the body temperature of about 37° C., or below about 20° C., but above the freezing temperature of about 0° C. This non-freezing thermal cooling may either slow nerve conduction or may cause direct neural injury. Slowed nerve conduction may use continuous or intermittent cooling of the target neural fibers to sustain the desired thermal neuromodulation, while direct neural injury may require only a discrete treatment to achieve sustained thermal neuromodulation. Thermal cooling for neuromodulation also may include freezing thermal nerve injury by reducing the temperature of the target neural fibers or of the vascular structures that feed the fibers to temperatures below the freezing point of about 0° C. Regardless of the type of cold exposure utilized to induce the thermal neuromodulation (freezing or non-freezing), a reduction in renal sympathetic nerve activity ("RSNA") is expected.

Figure 16:
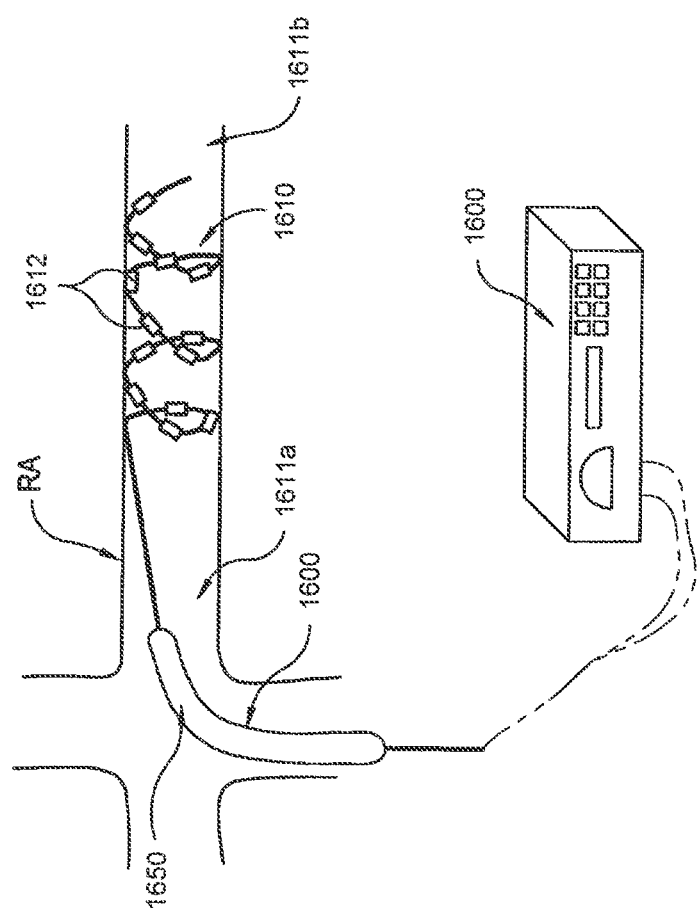
FIG. 16 is a schematic side-view, partially in section, of an intravascular catheter having a plurality of electrodes in accordance with one embodiment of the invention.

FIG. 16 shows one embodiment of an intravascular pulsed electric field apparatus 1600 in accordance with the present invention that includes one or more electrodes configured to physically contact a target region within the renal vasculature and deliver a pulsed electric field across a wall of the vasculature. The apparatus 1600 is shown within a patient's renal artery RA, but it can be positioned in other intravascular locations (e.g., the renal vein). This embodiment of the apparatus 1600 comprises an intravascular catheter 1610 having a proximal section 1611a, a distal section 1611b, and a plurality of distal electrodes 1612 at the distal section 1611b. The proximal section 1611a generally has an electrical connector to couple the catheter 1610 to a pulse generator, and the distal section 1611b in this embodiment has a helical configuration. The apparatus 1600 is electrically coupled to a pulsed electric field generator 1600 located proximal and external to the patient; the electrodes 1612 are electrically coupled to the generator via catheter 1610. The generator 1600 may be utilized with any embodiment of the present invention described hereinafter for delivery of a PEF with desired field parameters. It should be understood that electrodes of embodiments described hereinafter may be connected to the generator, even if the generator is not explicitly shown or described with each variation.

The helical distal section 1611b of catheter 1610 is configured to appose the vessel wall and bring electrodes 1612 into close proximity to extra-vascular neural structures. The pitch of the helix can be varied to provide a longer treatment zone, or to minimize circumferential overlap of adjacent treatments zones in order to reduce a risk of stenosis formation. This pitch change can be achieved by combining a plurality of catheters of different pitches to form catheter 1610, or by adjusting the pitch of catheter 1610 through the use of internal pull wires, adjusting mandrels inserted into the catheter, shaping sheaths placed over the catheter, or by any other suitable means for changing the pitch either in-situ or before introduction into the body.

The electrodes 1612 along the length of the pitch can be individual electrodes, a common but segmented electrode, or a common and continuous electrode. A common and continuous electrode may, for example, comprise a conductive coil formed into or placed over the helical portion of catheter 1610. A common but segmented electrode may, for example, be formed by providing a slotted tube fitted onto or into the helical portion of the catheter, or by electrically connecting a series of individual electrodes.

Individual electrodes or groups of electrodes 1612 may be configured to provide a bipolar signal, or all or a subset of the electrodes may be used together in conjunction with a separate external patient ground for monopolar use (the ground pad may, for example, be placed on the patient's leg). Electrodes 1612 may be dynamically assignable to facilitate monopolar and/or bipolar energy delivery between any of the electrodes and/or between any of the electrodes and an external ground.

Catheter 1610 may be delivered to renal artery RA in a low profile delivery configuration within sheath 1650. Once positioned within the artery, the catheter may self-expand or may be expanded actively, e.g., via a pull wire or a balloon, into contact with an interior wall of the artery. A pulsed electric field then may be generated by the PEF generator 1600, transferred through catheter 1610 to electrodes 1612, and delivered via the electrodes 1612 across the wall of the artery. In many applications, the electrodes are arranged so that the pulsed electric field is aligned with the longitudinal dimension of the artery to modulate the neural activity along the renal nerves (e.g., denervation). This may be achieved, for example, via irreversible electroporation, electrofusion and/or inducement of apoptosis in the nerve cells.

Figure 17:
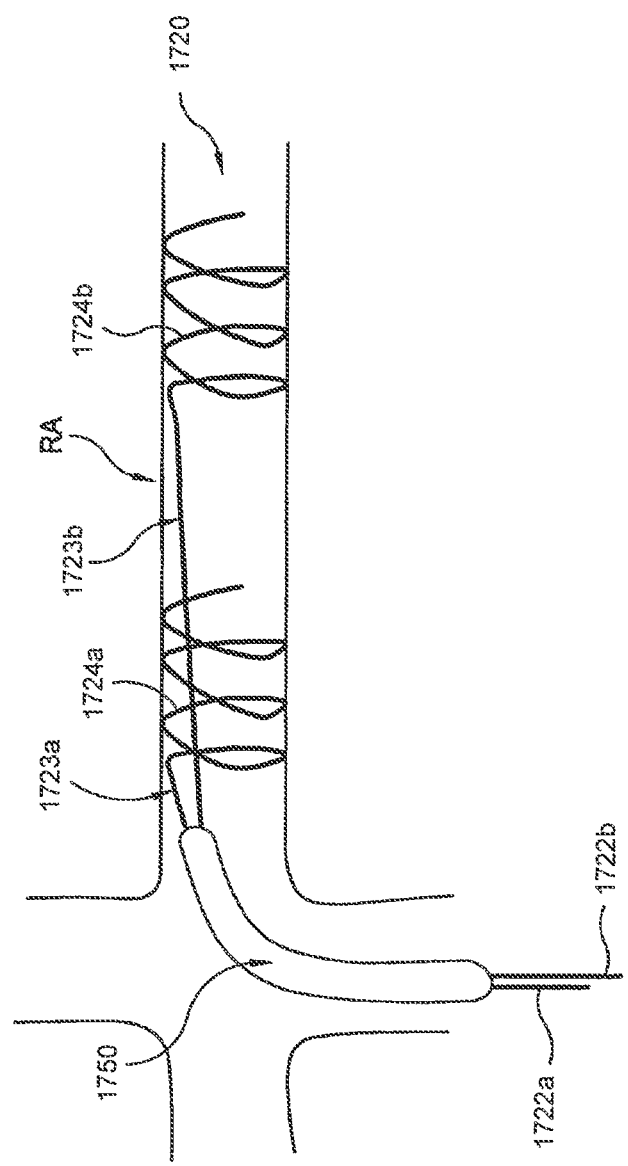
FIG. 17 is a schematic side-view, partially in section, of an intravascular device having a pair of expanding helical electrodes arranged at a desired distance from one another in accordance with another embodiment of the invention.

FIG. 17 illustrates an apparatus 1720 for neural modulation in accordance with another embodiment of the invention. The apparatus 1720 includes a pair of catheters 1722a and 1722b having expandable distal sections 1723a and 1723b with helical electrodes 1724a and 1724b, respectively. The helical electrodes 1724a and 1724b are spaced apart from each other by a desired distance within a patient's renal vasculature. Electrodes 1724a-b may be actuated in a bipolar fashion such that one electrode is an active electrode and the other is a return electrode. The distance between the electrodes may be altered as desired to change the field strength and/or the length of nerve segment modulated by the electrodes. The expandable helical electrodes may comprise shape-memory properties that facilitate self-expansion, e.g., after passage through sheath 1750, or the electrodes may be actively expanded into contact with the vessel wall, e.g., via an inflatable balloon or via pull wires, etc. The catheters 1722a-b preferably are electrically insulated in areas other than the distal helices of electrodes 1724a-b.

It is expected that thermally-induced renal neuromodulation, whether delivered extravascularly, intravascularly, intra-to-extravascularly or a combination thereof, may alleviate clinical symptoms of CHF, hypertension, renal disease, myocardial infarction, atrial fibrillation, contrast nephropathy and/or other cardio-renal diseases for a period of months, (potentially up to six months or more). This time period may be sufficient to allow the body to heal; for example, this period may reduce the risk of CHF onset after an acute myocardial infarction, to thereby alleviateing a need for subsequent re-treatment. Alternatively, as symptoms reoccur, or at regularly scheduled intervals, the patient may receive repeat therapy. Thermally-induced renal neuromodulation also may systemically reduce sympathetic tone.

Figure 18:
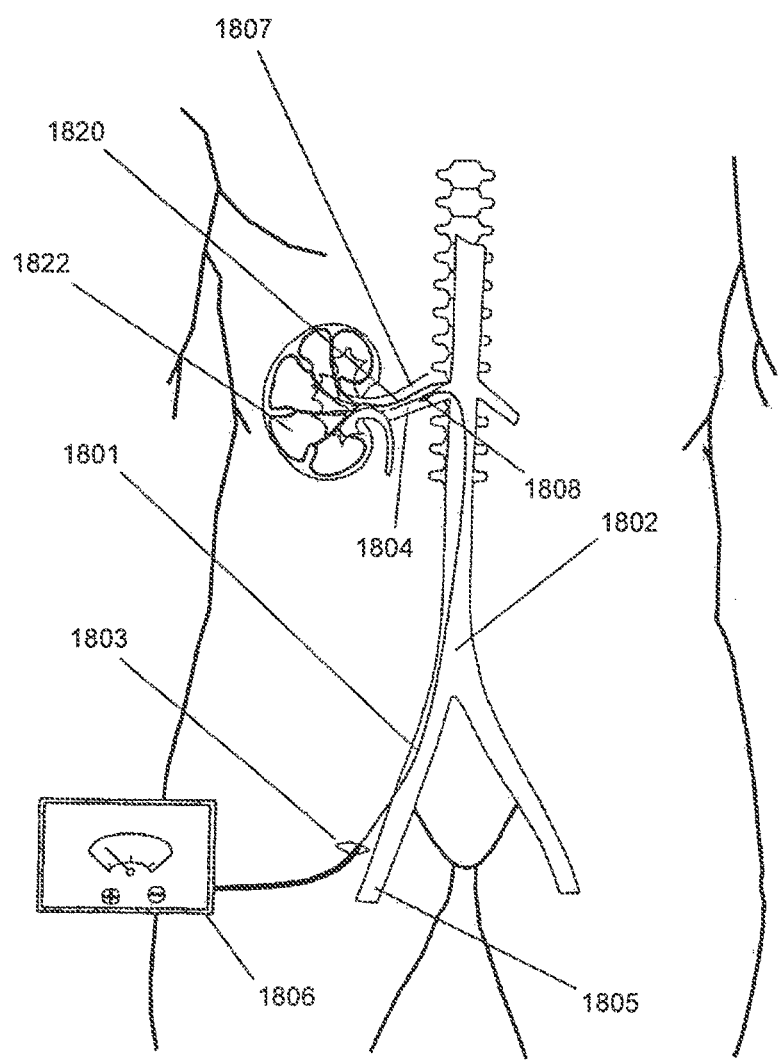
FIG. 18 illustrates stimulation of renal nerves across the wall of a renal vein.

FIG. 18 shows external renal nerve stimulator apparatus 1806 connected to the electrode tip 1808 by the catheter 1801. A catheter is inserted via an insertion site 1803 into the femoral vein 1805 into the vena cava 1802 and further into the renal vein 1804. The tip 1808 is then brought into the electric contact with the wall of the vein 1804. Hooks or screws, similar to ones used to secure pacemaker leads, can be used to anchor the tip and improve the electric contact. The tip 1808 can have one, two or more electrodes integrated in its design. The purpose of the electrodes is to generate the electric field sufficiently strong to influence traffic along the renal nerve 205 stimulating the kidney 208.

Two potential uses for the embodiment shown on FIG. 18 are the acute short-term stimulation of the renal nerve and the implanted embodiment. For short term treatment, a catheter equipped with electrodes on the tip is positioned in the renal vein. The proximal end of the catheter is left outside of the body and connected to the electro stimulation apparatus. For the implanted application, the catheter is used to position a stimulation lead, which is anchored in the vessel and left in place after the catheter is withdrawn. The lead is then connected to the implantable stimulator that is left in the body and the surgical site is closed. Patients have the benefit of mobility and lower risk of infection with the implanted stimulator—lead system.

Similar to the venous embodiment, an arterial system can be used. Catheter will be introduced via the femoral artery and aorta (not shown) into the renal artery 1807. Arterial catheterization is more dangerous than venous but may achieve superior result by placing stimulation electrode (or electrodes) in close proximity to the renal nerve without surgery.

Ablation of conductive tissue pathways is another commonly used technique to control aterial or ventricular tachycardia of the heart. Ablation can be performed by introduction of a catheter into the venous system in close proximity of the sympathetic renal nerve subsequent ablation of the tissue. Catheter based ablation devices were previously used to stop electric stimulation of nerves by heating nerve tissue with RF energy that can be delivered by a system of electrodes. RF energy thus delivered stops the nerve conduction. U.S. Pat. No. 6,292,695 describes in detail a method and apparatus for transvascular treatment of tachycardia and fibrillation with nerve stimulation and ablation. Similar catheter based apparatus can be used to ablate the renal nerve with an intent to treat CRF. The method described in this invention is applicable to irreversible ablation of the renal nerve by electric energy, cold, or chemical agents such as phenol or alcohol.

Thermal means may be used to cool the renal nerve and adjacent tissue to reduce the sympathetic nerve stimulation of the kidney. Specifically, the renal nerve signals may be dampened by either directly cooling the renal nerve or the kidney, to reduce their sensitivity, metabolic activity and function, or by cooling the surrounding tissue. An example of this approach is to use the cooling effect of the Peltier device. Specifically, the thermal transfer junction may be positioned adjacent the vascular wall or a renal artery to provide a cooling effect. The cooling effect may be used to dampen signals generated by the kidney. Another example of this approach is to use the fluid delivery device to deliver a cool or cold fluid (e.g. saline).

Figure 19A:
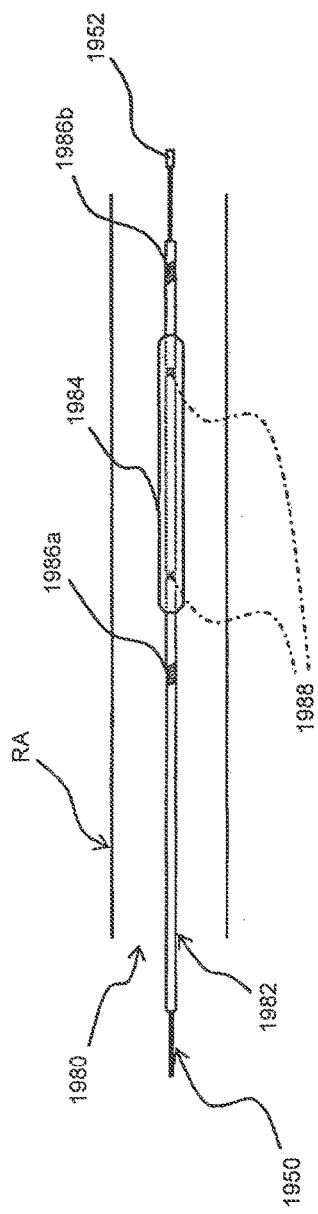
FIGS. 19A and 19B are side views, partially in section, illustrating an intravascular device having detectors for measuring or monitoring treatment efficacy in accordance with another embodiment of the invention.
Figure 19B:
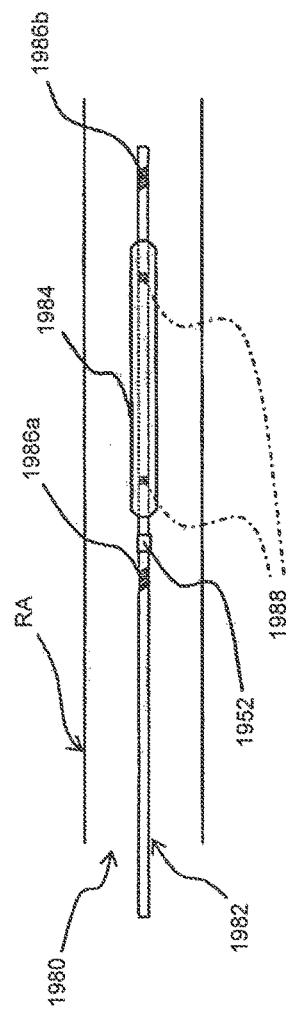

Referring to FIGS. 19A and 19B, variations of the invention comprising detectors or other elements for measuring or monitoring treatment efficacy are described. Variations of the invention may be configured to deliver stimulation electric fields, in addition to denervating or modulating PEFs. These stimulation fields may be utilized to properly position the apparatus for treatment and/or to monitor the effectiveness of treatment in modulating neural activity. This may be achieved by monitoring the responses of physiologic parameters known to be affected by stimulation of the renal nerves. Such parameters comprise, for example, renin levels, sodium levels, renal blood flow and blood pressure. Stimulation also may be used to challenge the denervation for monitoring of treatment efficacy: upon denervation of the renal nerves, the known physiologic responses to stimulation should no longer occur in response to such stimulation.

Efferent nerve stimulation waveforms may, for example, comprise frequencies of about 1-10 Hz, while afferent nerve stimulation waveforms may, for example, comprise frequencies of up to about 50 Hz. Waveform amplitudes may, for example, range up to about 50V, while pulse durations may, for example, range up to about 20 milliseconds. When the nerve stimulation waveforms are delivered intravascularly, as in several embodiments of the present invention, field parameters such as frequency, amplitude and pulse duration may be modulated to facilitate passage of the waveforms through the wall of the vessel for delivery to target nerves. Furthermore, although exemplary parameters for stimulation waveforms have been described, it should be understood that any alternative parameters may be utilized as desired.

The electrodes used to deliver PEFs in any of the previously described variations of the present invention also may be used to deliver stimulation waveforms to the renal vasculature. Alternatively, the variations may comprise independent electrodes configured for stimulation. As another alternative, a separate stimulation apparatus may be provided.

One way to use stimulation to identify renal nerves is to stimulate the nerves such that renal blood flow is affected—or would be affected if the renal nerves had not been denervated or modulated. Stimulation acts to reduce renal blood flow, and this response may be attenuated or abolished with denervation. Thus, stimulation prior to neural modulation would be expected to reduce blood flow, while stimulation after neural modulation would not be expected to reduce blood flow to the same degree when utilizing similar stimulation parameters and location(s) as prior to neural modulation. This phenomenon may be utilized to quantify an extent of renal neuromodulation. Variations of the present invention may comprise elements for monitoring renal blood flow or for monitoring any of the other physiological parameters known to be affected by renal stimulation.

In FIG. 19A, an apparatus 1980 to achieve renal denervation including an element for monitoring of renal blood flow is shown. Apparatus 1980 comprises catheter 1982 having optional inflatable balloon or centering element 1984, shaft electrodes 1986a and 286b disposed along the shaft of the catheter on either side of the balloon, as well as optional radiopaque markers 1988 disposed along the shaft of the catheter, illustratively in line with the balloon. Balloon 1984 serves as both a centering element for electrodes 1986 and as an electrical insulator for directing the electric field. Guidewire 1950 having Doppler ultrasound sensor 1952 has been advanced through the lumen of catheter 1982 for monitoring blood flow within renal artery RA. Doppler ultrasound sensor 1952 is configured to measure the velocity of flow through the artery. A flow rate then may be calculated according to the formula:

$$Q=VA$$

where Q equals flow rate, V equals flow velocity and A equals cross-sectional area. A baseline of renal blood flow may be determined via measurements from sensor 1952 prior to delivery of a stimulation waveform, then stimulation may be delivered between electrodes 1986, preferably with balloon 1984 deflated. Alteration of renal blood flow from the baseline, or lack thereof, may be monitored with sensor 1952 to identify optimal locations for neuromodulation and/or denervation of the renal nerves.

FIG. 19B illustrates a variation of the apparatus of FIG. 19A, wherein Doppler ultrasound sensor 1952 is coupled to the shaft of catheter 1982. Sensor 1952 illustratively is disposed proximal of balloon 1984, but it should be understood that the sensor alternatively may be disposed distal of the balloon.

In addition or as an alternative to intravascular monitoring of renal blood flow via Doppler ultrasound, such monitoring optionally may be performed from external to the patient whereby renal blood flow is visualized through the skin (e.g., using an ultrasound transducer). In another variation, one or more intravascular pressure transducers may be used to sense local changes in pressure that may be indicative of renal blood flow. As yet another alternative, blood velocity may be determined, for example, via thermodilution by measuring the time lag for an intravascular temperature input to travel between points of known separation distance.

For example, a thermocouple may be incorporated into, or provided in proximity to, each electrode 1986, and chilled (i.e., lower than body temperature) fluid or saline may be infused proximally of the thermocouple(s). A time lag for the temperature decrease to register between the thermocouple(s) may be used to quantify flow characteristic(s). A baseline estimate of the flow characteristic(s) of interest may be determined prior to stimulation of the renal nerves and may be compared with a second estimate of the characteristic(s) determined after stimulation.

Commercially available devices optionally may be utilized to monitor treatment. Such devices include, for example, the SmartWire™, FloWire™ and WaveWire™ devices available from Volcano™ Therapeutics Inc., of Rancho Cordova, Calif., as well as the PressureWire® device available from RADI Medical Systems AB of Uppsala, Sweden. Additional commercially available devices will be apparent. An extent of electroporation additionally or alternatively may be monitored directly using Electrical Impedance Tomography ("EIT") or other electrical impedance measurements, such as an electrical impedance index.

Although preferred illustrative variations of the present invention are described above, it will be apparent to those skilled in the art that various changes and modifications may be made thereto without departing from the invention. It is intended in the appended claims to cover all such changes and modifications that fall within the true spirit and scope of the invention.

We claim:

1. A method for renal neuromodulation of a human patient, the method comprising:
   intravascularly positioning a catheter within a renal artery of the human patient and proximate to neural fibers innervating a kidney of the patient, the catheter comprising a first infusion needle and a second infusion needle;
   deploying the first and second infusion needles to pierce a wall of the renal artery; and
   injecting a neuromodulatory agent through the first and second infusion needles to at least partially ablate the neural fibers innervating the kidney of the patient,
   wherein at least partially ablating the neural fibers blocks or reduces neural transmission along the neural fibers.

2. The method of claim 1, wherein the neuromodulatory agent comprises a drug or medicament.

3. The method of claim 1, wherein the neuromodulatory agent comprises a neurotoxin.

4. The method of claim 3, wherein the neuromodulatory agent comprises botulinum toxin.

5. The method of claim 1, wherein the catheter further comprises an expandable positioning element.

6. The method of claim 5, wherein the expandable positioning element comprises a balloon.

7. The method of claim 5, wherein the expandable positioning element comprises an expandable basket or cage.

8. The method of claim 5, further comprising expanding the expandable positioning element within the renal artery.

9. The method of claim 8, wherein deploying the first and second infusion needles further comprises deploying the first and second infusion needles after expanding the expandable positioning element within the renal artery.

10. The method of claim 1, further comprising deploying the first and second infusion needles approximately to the same depth within the renal artery wall.

11. The method of claim 1, further comprising alleviating clinical symptoms of hypertension in the human patient.

12. The method of claim 11, wherein the method comprises alleviating clinical symptoms of hypertension in the human patient for a period of up to six months or more.

13. The method of claim 1, further comprising alleviating clinical symptoms of chronic heart failure in the human patient.

14. The method of claim 1, further comprising alleviating clinical symptoms of renal disease in the human patient.

15. The method of claim 1, further comprising alleviating clinical symptoms of myocardial infarction in the human patient.

16. The method of claim 1, further comprising alleviating clinical symptoms of atrial fibrillation in the human patient.

17. The method of claim 1, wherein the catheter comprises a shaft having first and second side ports.

18. The method of claim 17, wherein deploying the first and second infusion needles comprises advancing the first infusion needle through the first side port and the second infusion needle through the second side port.

19. A method for renal neuromodulation of a human patient having clinical symptoms of hypertension, the method comprising:
   intravascularly advancing a catheter within a renal artery of the human patient and proximate to a renal nerve innervating a kidney of the patient, the catheter comprising a balloon and a plurality of infusion needles;
   expanding the balloon to position or center the catheter within the renal artery;
   deploying the plurality of infusion needles to pierce a wall of the renal artery;
   injecting a neuromodulatory agent through the plurality of infusion needles to at least partially ablate the renal nerve innervating the kidney and inhibit neural traffic along the renal nerve; and
   intravascularly removing the catheter from the renal artery after injecting the neuromodulatory agent,
   wherein the method comprises alleviating the clinical symptoms of hypertension in the human patient.

20. The method of claim 19, wherein deploying the plurality of infusion needles locates distal regions of the plurality of infusion needles extravascularly.

21. The method of claim 19, wherein the neuromodulatory agent comprises a drug or medicament.

22. The method of claim 19, wherein the method comprises alleviating the clinical symptoms of hypertension in the human patient for a period of up to six months or more.

23. The method of claim 19, wherein intravascularly advancing a catheter within a renal artery of the human patient comprises advancing the catheter over a guidewire.

24. The method of claim 19, wherein the catheter comprises a shaft having a plurality of side ports.

25. The method of claim 24, wherein deploying the plurality of infusion needles comprises advancing each of the plurality of infusion needles through a corresponding side port in the shaft of the catheter.

* * * * *